United States Patent
Bonrath et al.

(10) Patent No.: US 12,077,801 B2
(45) Date of Patent: Sep. 3, 2024

(54) REGIOSELECTIVE HYDROXYLATION OF ISOPHORONE

(71) Applicant: DSM IP Assets B.V., Heerlen (NL)

(72) Inventors: Werner Bonrath, Kaiseraugst (CH); Martin Schürmann, Geleen (NL); Michele Tavanti, Manchester (GB); Fabio Parmeggiani, Manchester (GB); Nicholas Turner, Manchester (GB); Andrea Mattevi, Pavia (IT); Jose Ruben Casstellanos, Pavia (IT)

(73) Assignee: DSM IP ASSETS B.V., Heerlen (NL)

( * ) Notice: Subject to any disclaimer, the term of this patent is extended or adjusted under 35 U.S.C. 154(b) by 1084 days.

(21) Appl. No.: 16/500,497

(22) PCT Filed: Apr. 6, 2018

(86) PCT No.: PCT/EP2018/058897
§ 371 (c)(1),
(2) Date: Oct. 3, 2019

(87) PCT Pub. No.: WO2018/185304
PCT Pub. Date: Oct. 11, 2018

(65) Prior Publication Data
US 2021/0108234 A1    Apr. 15, 2021

(30) Foreign Application Priority Data

Apr. 7, 2017    (EP) .................................. 17165528

(51) Int. Cl.
*C12P 7/26*    (2006.01)
*C12N 9/02*    (2006.01)

(52) U.S. Cl.
CPC .............. *C12P 7/26* (2013.01); *C12N 9/0081* (2013.01); *C12Y 114/15006* (2013.01)

(58) Field of Classification Search
None
See application file for complete search history.

(56) References Cited

U.S. PATENT DOCUMENTS 6,300,521 B1    10/2001    Klatt et al.

FOREIGN PATENT DOCUMENTS

| CN | 101417936 | 4/2009 |
| CN | 101595224 | 12/2009 |

(Continued)

OTHER PUBLICATIONS

Expasy (EXPasy Compute pI/Mw, Using SEQ ID 3, available at https://web.expasy.org/cgi-bin/compute_pi/pi_tool, accessed on Oct. 16, 2023 (Year: 2023).*

(Continued)

*Primary Examiner* — Robert J Yamasaki
*Assistant Examiner* — Charles Zoltan Constantine
(74) *Attorney, Agent, or Firm* — Nixon & Vanderbye, PC

(57) ABSTRACT

The present invention relates to novel process for the production of ketoisophorone via biocatalytic conversion of isophorone, in particular a one-pot biocatalytic system for conversion of α-isophorone in a two-step oxidation process, with a first oxidation being catalyzed by a heme containing oxidoreductase such as a cytochrome P450 monooxygenase followed by another oxidation which can be either a chemical reaction or a biocatalytic reaction, in particular wherein the oxidation is catalyzed by an NAD(P) or NADP(H)-dependent oxidoreductase. The invention further provides polypeptides and nucleic acid sequences coding for cytochrome P450 monooxygenase with modified (higher) substrate selectivity, total turnover numbers and/or (re) activity compared to the wild-type enzyme. Ketoisophorone (Continued)

Figure 1:
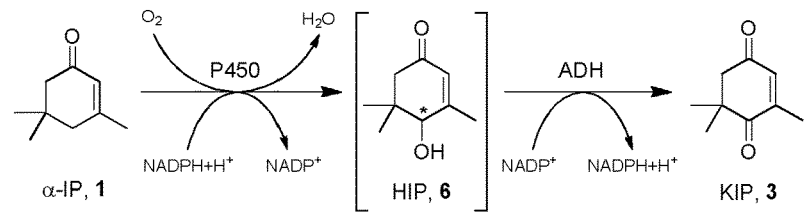
Figure 1:
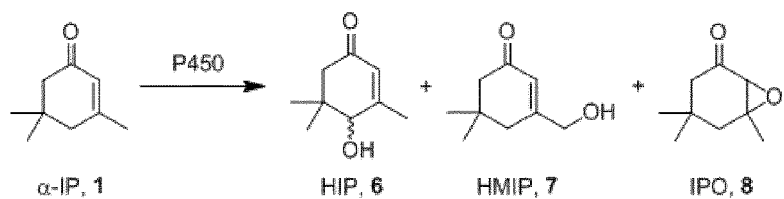
Figure 1:
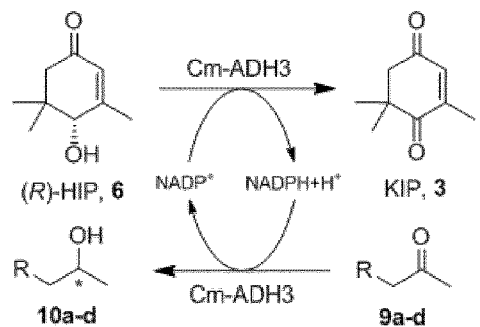
Figure 1:
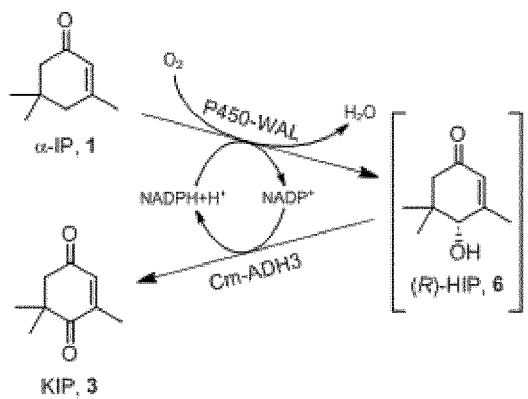

is useful as building block in the synthesis of vitamins and carotenoids.

12 Claims, 9 Drawing Sheets

Specification includes a Sequence Listing.

(56) References Cited

FOREIGN PATENT DOCUMENTS

| EP | 1 094 062 | 4/2001 |
|---|---|---|
| WO | 01/07630 | 2/2001 |
| WO | WO 2008/068030 | 6/2008 |

OTHER PUBLICATIONS

International Search Report for PCT/EP2018/058897, mailed Aug. 6, 2018, 9 pages.
Written Opinion of the ISA for PCT/EP2018/058897, mailed Aug. 6, 2018, 20 pages.
Kaluzna et al., "Enabling Selective and Sustainable P450 Oxygenation Technology. Production of 4-Hydroxy-α-isophorone on Kilogram Scale", Organic Process Research & Development, vol. 20, No. 4, Mar. 14, 2016, pp. 814-819 Beck et al., "Oxidation-Isomerization of an Olefin to Allylic Alcohol Using Titania-Silica and a Base Co-Catalyst", Journal of Catalysis, vol. 195, No. 1, Oct. 2000, pp. 79-87.
Beck et al., "Oxidation-Isomerization of an Olefin to Allylic Alcohol Using Titania-Silica and a Base Co-Catalyst", Journal of Catalysis, vol. 195, No. 1, Oct. 2000, pp. 79-87.
Kataoka et al., "Gene cloning of an NADPH-dependent menadione reductase from Candida macedoniensis, and its application to chiral alcohol production", Enzyme and Microbial Technology, vol. 38, No. 7, Oct. 10, 2005, pp. 944-951.
Kelly et al., "Active site diversification of P450cam with indole generates catalysts for benzylic oxidation reactions", Beilstein Journal of Organic Chemistry, vol. 11, Sep. 22, 2015, pp. 1713-1720, XP-002774152.
Kelly et al., "Supporting Information for Active site diversification of P450cam with indole generates catalysts for benzylic oxidation reactions", Sep. 22, 2015, 19 pages, XP-002774153.
Tavanti et al., "One-Pot Biocatalytic Double Oxidation of α-Isophorone for the Synthesis of Ketoisophorone", Chemcatchem, vol. 9, No. 17, Jul. 24, 2017, pp. 3338-3348.

\* cited by examiner

A:

B:

C:

D:

A:

B:

A:

B:

A:

B:

C:

SEQUENCE LISTING

```
<160> NUMBER OF SEQ ID NOS: 23

<210> SEQ ID NO 1
<211> LENGTH: 1049
<212> TYPE: PRT
<213> ORGANISM: Bacillus megaterium

<400> SEQUENCE: 1

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270
```

-continued

```
Leu Leu Ser Phe Ala Leu Tyr Phe Leu Val Lys Asn Pro His Val Leu
            275                 280                 285
Gln Lys Ala Ala Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
```

```
                690               695               700
Pro Arg Asn Tyr Glu Gly Ile Val Asn Arg Val Thr Ala Arg Phe Gly
705               710               715               720

Leu Asp Ala Ser Gln Gln Ile Arg Leu Glu Ala Glu Glu Lys Leu
              725               730               735

Ala His Leu Pro Leu Ala Lys Thr Val Ser Val Glu Leu Leu Gln
              740               745               750

Tyr Val Glu Leu Gln Asp Pro Val Thr Arg Thr Gln Leu Arg Ala Met
              755               760               765

Ala Ala Lys Thr Val Cys Pro Pro His Lys Val Glu Leu Glu Ala Leu
770               775               780

Leu Glu Lys Gln Ala Tyr Lys Glu Gln Val Leu Ala Lys Arg Leu Thr
785               790               795               800

Met Leu Glu Leu Leu Glu Lys Tyr Pro Ala Cys Glu Met Lys Phe Ser
              805               810               815

Glu Phe Ile Ala Leu Leu Pro Ser Ile Arg Pro Arg Tyr Tyr Ser Ile
              820               825               830

Ser Ser Ser Pro Arg Val Asp Glu Lys Gln Ala Ser Ile Thr Val Ser
              835               840               845

Val Val Ser Gly Glu Ala Trp Ser Gly Tyr Gly Glu Tyr Lys Gly Ile
850               855               860

Ala Ser Asn Tyr Leu Ala Glu Leu Gln Glu Gly Asp Thr Ile Thr Cys
865               870               875               880

Phe Ile Ser Thr Pro Gln Ser Glu Phe Thr Leu Pro Lys Asp Pro Glu
              885               890               895

Thr Pro Leu Ile Met Val Gly Pro Gly Thr Gly Val Ala Pro Phe Arg
              900               905               910

Gly Phe Val Gln Ala Arg Lys Gln Leu Lys Glu Gln Gly Gln Ser Leu
              915               920               925

Gly Glu Ala His Leu Tyr Phe Gly Cys Arg Ser Pro His Glu Asp Tyr
              930               935               940

Leu Tyr Gln Glu Glu Leu Glu Asn Ala Gln Ser Glu Gly Ile Ile Thr
945               950               955               960

Leu His Thr Ala Phe Ser Arg Met Pro Asn Gln Pro Lys Thr Tyr Val
              965               970               975

Gln His Val Met Glu Gln Asp Gly Lys Lys Leu Ile Glu Leu Leu Asp
              980               985               990

Gln Gly Ala His Phe Tyr Ile Cys Gly Asp Gly Ser Gln Met Ala Pro
              995               1000              1005

Ala Val Glu Ala Thr Leu Met Lys Ser Tyr Ala Asp Val His Gln
    1010              1015              1020

Val Ser Glu Ala Asp Ala Arg Leu Trp Leu Gln Gln Leu Glu Glu
    1025              1030              1035

Lys Gly Arg Tyr Ala Lys Asp Val Trp Ala Gly
    1040              1045

<210> SEQ ID NO 2
<211> LENGTH: 3150
<212> TYPE: DNA
<213> ORGANISM: Bacillus megaterium

<400> SEQUENCE: 2
atgacaatta aagaaatgcc tcagccaaaa acgtttggag agcttaaaaa tttaccgtta       60
ttaaacacag ataaaccggt tcaagctttg atgaaaattg cggatgaatt aggagaaatc      120
```

```
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag gagacgggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgttttaaca    2400 atgcttgaac tgcttgaaaa ataccccggcg tgtgaaatga aattcagcga atttatcgcc    2460
```

-continued

```
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaggc    3120 cgatacgcaa agacgtgtg ggctgggtaa                                      3150
```

<210> SEQ ID NO 3
<211> LENGTH: 752
<212> TYPE: PRT
<213> ORGANISM: Artificial Sequence
<220> FEATURE:
<223> OTHER INFORMATION: chimeric P450

<400> SEQUENCE: 3

```
Met Gly Thr Glu Thr Ile Gln Ser Asn Ala Asn Leu Ala Pro Leu Pro
1               5                   10                  15

Pro His Val Pro Glu His Leu Val Phe Asp Phe Asp Met Tyr Asn Pro
                20                  25                  30

Ser Asn Leu Ser Ala Gly Val Gln Glu Ala Trp Ala Val Leu Gln Glu
            35                  40                  45

Ser Asn Val Pro Asp Leu Val Trp Thr Arg Cys Asn Gly Gly His Trp
        50                  55                  60

Ile Ala Thr Arg Gly Gln Leu Ile Arg Glu Ala Tyr Glu Asp Tyr Arg
65                  70                  75                  80

His Phe Ser Ser Glu Cys Pro Phe Ile Pro Arg Glu Ala Gly Glu Ala
                85                  90                  95

Phe Asp Phe Ile Pro Thr Ser Met Asp Pro Pro Glu Gln Arg Gln Phe
            100                 105                 110

Arg Ala Leu Ala Asn Gln Val Val Gly Met Pro Val Val Asp Lys Leu
        115                 120                 125

Glu Asn Arg Ile Gln Glu Leu Ala Cys Ser Leu Ile Glu Ser Leu Arg
    130                 135                 140

Pro Gln Gly Gln Cys Asn Phe Thr Glu Asp Tyr Ala Glu Pro Phe Pro
145                 150                 155                 160

Ile Arg Ile Phe Met Leu Leu Ala Gly Leu Pro Glu Glu Asp Ile Pro
                165                 170                 175

His Leu Lys Tyr Leu Thr Asp Gln Met Thr Arg Pro Asp Gly Ser Met
            180                 185                 190

Thr Phe Ala Glu Ala Lys Glu Ala Leu Tyr Asp Tyr Leu Ile Pro Ile
        195                 200                 205

Ile Glu Gln Arg Arg Gln Lys Pro Gly Thr Asp Ala Ile Ser Ile Val
    210                 215                 220

Ala Asn Gly Gln Val Asn Gly Arg Pro Ile Thr Ser Asp Glu Ala Lys
225                 230                 235                 240
```

```
Arg Met Cys Gly Leu Leu Val Gly Gly Leu Asp Thr Val Val Asn
            245                 250                 255

Phe Leu Ser Phe Ser Met Glu Phe Leu Ala Lys Ser Pro Glu His Arg
        260                 265                 270

Gln Glu Leu Ile Glu Arg Pro Glu Arg Ile Pro Ala Ala Cys Glu Glu
            275                 280                 285

Leu Leu Arg Arg Phe Ser Leu Val Ala Asp Gly Arg Ile Leu Thr Ser
        290                 295                 300

Asp Tyr Glu Phe His Gly Val Gln Leu Lys Lys Gly Asp Gln Ile Leu
305                 310                 315                 320

Leu Pro Gln Met Leu Ser Gly Leu Asp Glu Arg Glu Asn Ala Ala Pro
                325                 330                 335

Met His Val Asp Phe Ser Arg Gln Lys Val Ser His Thr Thr Phe Gly
                340                 345                 350

His Gly Ser His Leu Cys Leu Gly Gln His Leu Ala Arg Arg Glu Ile
            355                 360                 365

Ile Val Thr Leu Lys Glu Trp Leu Thr Arg Ile Pro Asp Phe Ser Ile
        370                 375                 380

Ala Pro Gly Ala Gln Ile Gln His Lys Ser Gly Ile Val Ser Gly Val
385                 390                 395                 400

Gln Ala Leu Pro Leu Val Trp Asp Pro Ala Thr Thr Lys Ala Val His
                405                 410                 415

Met Arg Leu Ala Ser Thr His Met Leu His Arg His Gln Pro Val Thr
                420                 425                 430

Ile Gly Glu Pro Ala Ala Arg Ala Val Ser Arg Thr Val Thr Val Glu
            435                 440                 445

Arg Leu Asp Arg Ile Ala Asp Asp Val Leu Arg Leu Val Leu Arg Asp
        450                 455                 460

Ala Gly Gly Lys Thr Leu Pro Thr Trp Thr Pro Gly Ala His Ile Asp
465                 470                 475                 480

Leu Asp Leu Gly Ala Leu Ser Arg Gln Tyr Ser Leu Cys Gly Ala Pro
                485                 490                 495

Asp Ala Pro Ser Tyr Glu Ile Ala Val His Leu Asp Pro Glu Ser Arg
                500                 505                 510

Gly Gly Ser Arg Tyr Ile His Glu Gln Leu Glu Val Gly Ser Pro Leu
            515                 520                 525

Arg Met Arg Gly Pro Arg Asn His Phe Ala Leu Asp Pro Gly Ala Glu
        530                 535                 540

His Tyr Val Phe Val Ala Gly Gly Ile Gly Ile Thr Pro Val Leu Ala
545                 550                 555                 560

Met Ala Asp His Ala Arg Ala Arg Gly Trp Ser Tyr Glu Leu His Tyr
                565                 570                 575

Cys Gly Arg Asn Arg Ser Gly Met Ala Tyr Leu Glu Arg Val Ala Gly
                580                 585                 590

His Gly Asp Arg Ala Ala Leu His Val Ser Glu Glu Gly Thr Arg Ile
            595                 600                 605

Asp Leu Ala Ala Leu Leu Ala Glu Pro Ala Pro Gly Val Gln Ile Tyr
        610                 615                 620

Ala Cys Gly Pro Gly Arg Leu Leu Ala Gly Leu Glu Asp Ala Ser Arg
625                 630                 635                 640

Asn Trp Pro Asp Gly Ala Leu His Val Glu His Phe Thr Ser Ser Leu
                645                 650                 655

Ala Ala Leu Asp Pro Asp Val Glu His Ala Phe Asp Leu Glu Leu Arg
```

```
                      660                 665                 670
Asp Ser Gly Leu Thr Val Arg Val Glu Pro Thr Gln Thr Val Leu Asp
            675                 680                 685

Ala Leu Arg Ala Asn Asn Ile Asp Val Pro Ser Asp Cys Glu Glu Gly
        690                 695                 700

Leu Cys Gly Ser Cys Glu Val Ala Val Leu Asp Gly Glu Val Asp His
705                 710                 715                 720

Arg Asp Thr Val Leu Thr Lys Ala Glu Arg Ala Asn Arg Gln Met
                725                 730                 735

Met Thr Cys Cys Ser Arg Ala Cys Gly Asp Arg Leu Ala Leu Arg Leu
            740                 745                 750

<210> SEQ ID NO 4
<211> LENGTH: 5678
<212> TYPE: DNA
<213> ORGANISM: Artificial Sequence
<220> FEATURE:
<223> OTHER INFORMATION: chimeric P450

<400> SEQUENCE: 4
```

| | |
|---|---|
| ggggaattgt gagcggataa caattcccct gtagaaataa ttttgtttaa ctttaataag | 60 |
| gagatatacc atgggcactg aaaccataca aagcaacgcc aatcttgccc ctctgccacc | 120 |
| ccatgtgcca gagcacctgg tattcgactt cgacatgtac aatccgtcga atctgtctgc | 180 |
| cggcgtgcag gaggcctggg cagttctgca agaatcaaac gtaccggatc tggtgtggac | 240 |
| tcgctgcaac ggcggacact ggatcgccac tcgcggccaa ctgatccgtg aggcctatga | 300 |
| agattaccgc cactttttcca gcgagtgccc gtggatccct cgtgaagccg cgaagccttt | 360 |
| tgacttcatt cccaccctcga tggatccgcc cgagcagcgc cagtttcgtg cgctggccaa | 420 |
| ccaagtggtt ggcatgccgg tggtggataa gctggagaac cggatccagg agctggcctg | 480 |
| ctcgctgatc gagagcctgc gcccgcaagg acagtgcaac ttcaccgagg actacgccga | 540 |
| acccttcccg atacgcatct tcatgctgct cgcaggtcta ccggaagaag atatcccgca | 600 |
| cttgaaatac ctaacggatc agatgacccg tccggatggc agcatgacct tcgcagaggc | 660 |
| caaggaggcg ctctacgact atctgatacc gatcatcgag caacgcaggc agaagccggg | 720 |
| aaccgacgct atcagcatcg ttgccaacgg ccaggtcaat gggcgaccga tcaccagtga | 780 |
| cgaagccaag aggatgtgtg cgcgttact gctcggcggc ctggatacgg tggtcaattt | 840 |
| cctcagcttc agcatggagt tcctggccaa aagcccggag catcgccagg agctgatcga | 900 |
| gcgtcccgag cgtattccag ccgcttgcga ggaactactc cggcgcttct cgctggttgc | 960 |
| cgatggccgc atcctcacct ccgattacga gtttcatggc gtgcaactga agaaaggtga | 1020 |
| ccagatcctg ctaccgcaga tgctgtctgg cctggatgag cgcgaaaacg ccgccccgat | 1080 |
| gcacgtcgac ttcagtcgcc aaaaggtttc acacaccacc tttggccacg cagccatct | 1140 |
| gtgccttggc cagcacctgg cccgccggga atcatcgtc accctcaagg aatggctgac | 1200 |
| caggattcct gacttctcca ttgccccggg tgcccagatt cagcacaaga gcggcatcgt | 1260 |
| cagcggcgtg caggcactcc ctctggtctg ggatccggcg actaccaaag cggtacatat | 1320 |
| gcgattggcc tccacgcata tgctgcaccg gcatcaaccg tcaccatcg agaacccgc | 1380 |
| cgcccgggcg gtgtcccgca ccgtcaccgt cgagcgcctg accggatcg ccgacgacgt | 1440 |
| gctgcgcctc gtcctgcgcg acgccggcgg aaagacatta cccacgtgga ctccggcgc | 1500 |
| ccatatcgac ctcgacctcg gcgcgctgtc cgcgccagtac tccctgtgcg gcgcgcccga | 1560 |

```
tgcgccgagc tacgagattg ccgtgcacct ggatcccgag agccgcggcg gttcgcgcta    1620
catccacgaa cagctcgagg tgggaagccc gctccggatg cgcggccctc ggaaccattt    1680
cgcgctcgac cccggcgccg agcactacgt gttcgtcgcc ggcggcatcg gcatcacccc    1740
agtcctggcg atggccgacc acgcccgcgc ccggggggtgg agctacgaac tgcactactg    1800
cggccgaaac cgttccggca tggcctatct cgagcgtgtc gccgggcacg gtgaccgggc    1860
cgccctgcac gtgtccgagg aaggcacccg gatcgacctc gccgccctcc tcgccgagcc    1920
cgcccccggc gtccagatct acgcgtgcgg gcccgggcgg ctgctcgccg gactcgagga    1980
cgcgagccgg aactggcccg acggggcgct gcacgtcgag cacttcacct cgtccctcgc    2040
ggcgctcgat ccggacgtcg agcacgcctt cgacctcgaa ctgcgtgact cggggctgac    2100
cgtgcgggtc gaacccaccc agaccgtcct cgacgcgttg cgcgccaaca acatcgacgt    2160
gcccagcgac tgcgaggaag gcctctgcgg ctcgtgcgag gtcgccgtcc tcgacggcga    2220
ggtcgaccat cgcgacacgg tgctgaccaa ggccgagcgg gcggcgaacc ggcagatgat    2280
gacctgctgc tcgcgtgcct gtggcgaccg gctggccctg cgactctgac ctaggctgct    2340
gccaccgctg agcaataact agcataaccc cttgggcct ctaaacgggt cttgaggggt    2400
tttttgctga aacctcaggc atttgagaag cacacggtca cactgcttcc ggtagtcaat    2460
aaaccggtaa accagcaata gacataagcg gctatttaac gaccctgccc tgaaccgacg    2520
accgggtcat cgtggccgga tcttgcgcc cctcggcttg aacgaattgt tagacattat    2580
ttgccgacta ccttggtgat ctcgcctttc acgtagtgga caaattcttc caactgatct    2640
gcgcgcgagg ccaagcgatc ttcttcttgt ccaagataag cctgtctagc ttcaagtatg    2700
acgggctgat actgggccgg caggcgctcc attgcccagt cggcagcgac atccttcggc    2760
gcgattttgc cggttactgc gctgtaccaa atgcgggaca acgtaagcac tacatttcgc    2820
tcatcgccag cccagtcggg cggcgagttc catagcgtta aggtttcatt tagcgcctca    2880
aatagatcct gttcaggaac cggatcaaag agttcctccg ccgctggacc taccaaggca    2940
acgctatgtt ctcttgcttt tgtcagcaag atagccagat caatgtcgat cgtggctggc    3000
tcgaagatac ctgcaagaat gtcattgcgc tgccattctc caaattgcag ttcgcgctta    3060
gctggataac gccacggaat gatgtcgtcg tgcacaacaa tggtgacttc tacagcgcgg    3120
agaatctcgc tctctccagg ggaagccgaa gtttccaaaa ggtcgttgat caaagctcgc    3180
cgcgttgttt catcaagcct tacggtcacc gtaaccagca aatcaatatc actgtgtggc    3240
ttcaggccgc catccactgc ggagccgtac aaatgtacgg ccagcaacgt cggttcgaga    3300
tggcgctcga tgacgccaac tacctctgat agttgagtcg atacttcggc gatcaccgct    3360
tccctcatac tcttccttt tcaatattat tgaagcattt atcagggtta ttgtctcatg    3420
agcggataca tatttgaatg tatttagaaa aataaacaaa tagctagctc actcggtcgc    3480
tacgctccgg gcgtgagact gcggcgggcg ctgcggacac atacaaagtt acccacagat    3540
tccgtggata agcaggggac taacatgtga ggcaaaacag cagggccgcg ccggtggcgt    3600
ttttccatag gctccgccct cctgccagag ttcacataaa cagacgcttt tccggtgcat    3660
ctgtgggagc cgtgaggctc aaccatgaat ctgacagtac gggcgaaacc cgacaggact    3720
taaagatccc caccgtttcc ggcgggtcgc tccctcttgc gctctcctgt tccgaccctg    3780
ccgtttaccg gatacctgtt ccgcctttct cccttacggg aagtgtggcg ctttctcata    3840
gctcacacac tggtatctcg gctcggtgta ggtcgttcgc tccaagctgg gctgtaagca    3900
agaactcccc gttcagcccg actgctgcgc cttatccggt aactgttcac ttgagtccaa    3960
```

-continued

```
cccggaaaag cacggtaaaa cgccactggc agcagccatt ggtaactggg agttcgcaga    4020
ggatttgttt agctaaacac gcggttgctc ttgaagtgtg cgccaaagtc cggctacact    4080
ggaaggacag atttggttgc tgtgctctgc gaaagccagt taccacggtt aagcagttcc    4140
ccaactgact taaccttcga tcaaaccacc tccccaggtg ttttttcgt ttacagggca     4200 aaagattacg cgcagaaaaa aaggatctca agaagatcct tgatctttt ctactgaacc     4260 gctctagatt tcagtgcaat ttatctcttc aaatgtagca cctgaagtca gccccatacg    4320
atataagttg taattctcat gttagtcatg ccccgcgccc accggaagga gctgactggg    4380
ttgaaggctc tcaagggcat cggtcgagat cccggtgcct aatgagtgag ctaacttaca    4440
ttaattgcgt tgcgctcact gcccgctttc cagtcgggaa acctgtcgtg ccagctgcat    4500
taatgaatcg gccaacgcgc ggggagaggc ggtttgcgta ttgggcgcca gggtggtttt    4560
tcttttcacc agtgagacgg gcaacagctg attgcccttc accgcctggc cctgagagag    4620
ttgcagcaag cggtccacgc tggtttgccc cagcaggcga aaatcctgtt tgatggtggt    4680
taacggcggg atataacatg agctgtcttc ggtatcgtcg tatcccacta ccgagatgtc    4740
cgcaccaacg cgcagcccgg actcggtaat ggcgcgcatt cgcccagcg ccatctgatc      4800 gttggcaacc agcatcgcag tgggaacgat gccctcattc agcatttgca tggtttgttg    4860
aaaaccggac atggcactcc agtcgccttc ccgttccgct atcggctgaa tttgattgcg    4920
agtgagatat ttatgccagc cagccagacg cagacgcgcc gagacagaac ttaatgggcc    4980
cgctaacagc gcgatttgct ggtgacccaa tgcgaccaga tgctccacgc ccagtcgcgt    5040
accgtcttca tgggagaaaa taatactgtt gatgggtgtc tggtcagaga catcaagaaa    5100
taacgccgga acattagtgc aggcagcttc cacagcaatg gcatcctggt catccagcgg    5160
atagttaatg atcagcccac tgacgcgttg cgcgagaaga ttgtgcaccg ccgctttaca    5220
ggcttcgacg ccgcttcgtt ctaccatcga caccaccacg ctggcaccca gttgatcggc    5280
gcgagattta atcgccgcga caatttgcga cggcgcgtgc agggccagac tggaggtggc    5340
aacgccaatc agcaacgact gtttgcccgc cagttgttgt gccacgcggt tgggaatgta    5400
attcagctcc gccatcgccg cttccacttt ttcccgcgtt ttcgcagaaa cgtggctggc    5460
ctggttcacc acgcgggaaa cggtctgata agagacaccg gcatactctg cgacatcgta    5520
taacgttact ggtttcacat tcaccaccct gaattgactc tcttccgggc gctatcatgc    5580
cataccgcga aaggttttgc gccattcgat ggtgtccggg atctcgacgc tctcccttat    5640
gcgactcctg cattaggaaa ttaatacgac tcactata                            5678
```

<210> SEQ ID NO 5
<211> LENGTH: 241
<212> TYPE: PRT
<213> ORGANISM: Candida magnoliae

<400> SEQUENCE: 5

Met Thr Thr Thr Ser Asn Ala Leu Val Thr Gly Gly Ser Arg Gly Ile
1               5                   10                  15

Gly Ala Ala Ser Ala Ile Lys Leu Ala Gln Glu Gly Tyr Ser Val Thr
            20                  25                  30

Leu Ala Ser Arg Ser Val Asp Lys Leu Asn Glu Val Lys Ala Lys Leu
        35                  40                  45

Pro Ile Val Gln Asp Gly Gln Lys His Tyr Ile Trp Glu Leu Asp Leu
    50                  55                  60

```
Ala Asp Val Glu Ala Ala Ser Ser Phe Lys Gly Ala Pro Leu Pro Ala
 65                  70                  75                  80

Ser Ser Tyr Asp Val Phe Val Ser Asn Ala Gly Val Ala Ala Phe Ser
                 85                  90                  95

Pro Thr Ala Asp His Asp Lys Glu Trp Gln Asn Leu Leu Ala Val
            100                 105                 110

Asn Leu Ser Ser Pro Ile Ala Leu Thr Lys Ala Leu Leu Lys Asp Val
            115                 120                 125

Ser Glu Arg Pro Ala Asp Asn Pro Leu Gln Ile Ile Tyr Ile Ser Ser
    130                 135                 140

Val Ala Gly Leu His Gly Ala Ala Gln Val Ala Val Tyr Ser Ala Ser
145                 150                 155                 160

Lys Ala Gly Leu Asp Gly Phe Met Arg Ser Val Ala Arg Glu Val Gly
                165                 170                 175

Pro Lys Gly Ile His Val Asn Ser Ile Asn Pro Gly Tyr Thr Lys Thr
            180                 185                 190

Glu Met Thr Ala Gly Ile Glu Ala Leu Pro Asp Leu Pro Ile Lys Gly
        195                 200                 205

Trp Ile Glu Pro Glu Ala Ile Ala Asp Ala Val Leu Phe Leu Ala Lys
    210                 215                 220

Ser Lys Asn Ile Thr Gly Thr Asn Ile Val Val Asp Asn Gly Leu Ile
225                 230                 235                 240

Ala

<210> SEQ ID NO 6
<211> LENGTH: 586
<212> TYPE: DNA
<213> ORGANISM: Candida magnoliae

<400> SEQUENCE: 6
actcccaatt gtacaggacg ggcagaagca ctacatttgg gaactcgatc tggctgatgt      60
ggaagctgct tcgtcgttca agggtgctcc tttgcctgct agcagctacg acgtcttcgt     120
ttcgaacgcg ggcgtcgctg cgttctcgcc cacagccgac cacgatgata aggagtggca     180
gaacttgctc gccgtgaact tgtcgtcgcc cattgccctc acgaaggccc tcttgaagga     240
cgtctccgaa aggcctgcgg acaatccgtt gcagattatc tacatttcgt cggtggccgg     300
cttgcatggc gccgcgcagg tcgccgtgta cagtgcatct aaggccggtc ttgatggttt     360
tatgcgctcc gtcgcccgtg aggtgggccc gaagggcatc catgtgaact ccatcaaccc     420
cggatacacc aagactgaaa tgaccgcggg cattgaagcc ctgcctgatt gcctatcaa     480 ggggtggatc gagcccgagg caattgctga cgcggttctg tttctggcaa agtccaagaa     540
tatcaccggc acaaacattg tggtcgacaa tggcttgatt gcttag                    586

<210> SEQ ID NO 7
<211> LENGTH: 343
<212> TYPE: PRT
<213> ORGANISM: Sporidiobolus salmonicolor

<400> SEQUENCE: 7

Met Ala Lys Ile Asp Asn Ala Val Leu Pro Glu Gly Ser Leu Val Leu
  1               5                  10                  15

Val Thr Gly Ala Asn Gly Phe Val Ala Ser His Val Val Glu Gln Leu
                 20                  25                  30

Leu Glu His Gly Tyr Lys Val Arg Gly Thr Ala Arg Ser Ala Ser Lys
             35                  40                  45
```

Leu Ala Asn Leu Gln Lys Arg Trp Asp Ala Lys Tyr Pro Gly Arg Phe
50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
                100                 105                 110

Leu Asn Ala Leu Arg Ala Ala Ala Thr Pro Ser Val Lys Arg Phe
                115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Asn Tyr
                195                 200                 205

Thr Ile Gly Thr Ile Phe Asp Pro Glu Thr Gln Ser Gly Ser Thr Ser
210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
                260                 265                 270

Gly Thr Ala Gly Thr Phe Asp Trp Asn Thr Val Leu Ala Thr Phe Arg
                275                 280                 285

Lys Leu Tyr Pro Ser Lys Thr Phe Pro Ala Asp Phe Pro Asp Gln Gly
                290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
                340

<210> SEQ ID NO 8
<211> LENGTH: 1375
<212> TYPE: DNA
<213> ORGANISM: Sporidiobolus salmonicolor

<400> SEQUENCE: 8
atggccaaaa tcgacaacgc tgtgcttccc gagggctcgc tcgtgctcgt caccggcgcc      60
aacggtgcgc cttccttgcc accacttccg gcctgggacg cggcgctcat gctcgtcgca     120
tacaggcttc gtcgcttcgc acgtcgtcga acagctcctt gaacacggtt acaaggtccg     180
tggtacggct cgtagtgcct ccaaacttgc caacctgcag aagcgctggg atgccaagta     240
ccccggtcgc ttcgagacgg ccgtggtcga ggacatgctc aaacagggag cttacgacga     300
agtgatcaag ggtgagtatc ttccccatct atttctccac ataagggcga gctgaccaga     360
gcggaccagc acaggcgccg ccggagttgc gcacatcgct tccgtcgtgt ccttctcgaa     420

```
caagtacgac gaggttgtca cccccgccat cggaggcacc ctcaacgctc tccgtgccgc    480
cgctgccacg ccctctgtca agcgcttcgt cctcacctcc tcgaccgttt cagcgcttat    540
ccccaagccg aatgtcgagg ggatctacct cgacgagaag tcctggaacc tcgagagcat    600
cgacaaggcc aagactctcc ctgaaagcga cccccagaag tcgctctggg tctacgccgc    660
gagcaagacc gaggcggagc ttgccgcttg gaaattcatg gacgagaaca aggtgcgcgt    720
ccttcctacc gtcctcccct tcctccctcc ttccttcctt ccttcgttcc cacgcatttc    780
ctacccccat ctcgcttctt ttaccgtttc gttgcctggt cgcctctcgc tcattcactc    840
tgaacggtcg gtctacgcct ccagccgca cttcacccte aacgccgtcc tccccaacta    900
cacgattggg acgatcttcg accccgagac ccagtccggc tcgacttcgg gctggatgat    960
gagtctcttc aatggcgaag tttccccgc cctcgtctg atgcccctc gtgagccttc    1020 tcatctgcag ttattccctc ccctctttca atgctgactt tctggcgagc ttacagagta   1080
ctacgtgtcg gccgtcgaca ttggtctcct gcacctcggg tgcttggttc tgccccagat   1140
cgagcgccgc cgcgtctacg gcaccgccgg cacgttcgac tggaacacgg tcctcgcgac   1200
gttccgcaag ctgtacccga gcaagacgtt cccggccgac ttccccgacc agggccagga   1260
cctctccaag ttcgacacgg ccccgagcct cgagatcctc aagagtttgg gcaggcccgg   1320
gtggaggtcg atcgaggaga gcatcaagga cctcgtcggc tccgaaaccg cttga        1375
```

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
gagtgcccgt ggatccctcg tgaagc                                          26

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gctggaaaag tggcggtaat c                                               21

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
aggatgtgtg gcgcgttact ggtcggc                                         27

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
cttggcttcg tcactggtga tcg                                            23

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
aggatgtgtg gcgcgttact gctcggcggc ctggatac                            38

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
tagtctccta ggtcagagtc gcagggccag cc                                  32

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
tcgtctctta agtcagagtc gcagggccag cc                                  32

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16
taatacgact cactataggg agaccacaac gg                                  32

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
acgtagcata tgacgactac ttcaaacgcg cttgtc                              36

<210> SEQ ID NO 18
<211> LENGTH: 41
<212> TYPE: DNA
<213> ORGANISM: Artificial Sequence
<220> FEATURE:
<223> OTHER INFORMATION: primer

<400> SEQUENCE: 18
atgctaccat ggggatgacg actacttcaa acgcgcttgt c                        41

<210> SEQ ID NO 19
<211> LENGTH: 34
<212> TYPE: DNA
<213> ORGANISM: Artificial Sequence -continued

```
<220> FEATURE:
<223> OTHER INFORMATION: primer

<400> SEQUENCE: 19
atgtatctta agcaatcaag ccattgtcga ccac                    34

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20
acgtcactcg agttaagcaa tcaagccatt gtcgaccac               39

<210> SEQ ID NO 21
<211> LENGTH: 39
<212> TYPE: DNA
<213> ORGANISM: Artificial Sequence
<220> FEATURE:
<223> OTHER INFORMATION: primer

<400> SEQUENCE: 21
agtcagccta ggttaagcaa tcaagccatt gtcgaccac               39

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
ctggatcata tggccaaaat cgataatgcc gtg                     33

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23
tgcatgctcg agttaggctg tttcgctacc aaccagg                 37
```

REGIOSELECTIVE HYDROXYLATION OF ISOPHORONE

This application is the U.S. national phase of International Application No. PCT/EP2018/058897 filed 6 Apr. 2018, which designated the U.S. and claims priority to EP Patent Application No. 17165528.5 filed 7 Apr. 2017, the entire contents of each of which are hereby incorporated by reference.

The present invention relates to novel process for the production of ketoisophorone via biocatalytic conversion of isophorone, in particular a one-pot biocatalytic system for conversion of α-isophorone in a two-step oxidation process, with a first oxidation being catalyzed by a heme containing oxidoreductase such as a cytochrome P450 monooxygenase followed by another oxidation which can be either a chemical reaction or a biocatalytic reaction, in particular wherein the oxidation is catalyzed by an NAD(P) or NADP(H)-dependent oxidoreductase. The invention further provides polypeptides and nucleic acid sequences coding for cytochrome P450 monooxygenase with modified (higher) substrate selectivity, total turnover numbers and/or (re) activity compared to the wild-type enzyme. Ketoisophorone is useful as building block in the synthesis of vitamins and carotenoids.

Monooxygenated terpenoids such as e.g. isophorone are relevant target compounds for the synthesis of active pharmaceutical ingredients (APIs), fragrances and nutritional supplements, e.g. vitamins. An example of such a target compound is ketoisophorone (2,6,6-trimethylcyclohex-2-ene-1,4-dione; KIP) which can be synthesized by oxidation of isophorone (IP). KIP can be further isomerized to trimethylhydroquinone (TMHQ), the key building block in the synthesis of vitamin E (for more detail see e.g. Ullmann's Encyclopedia of Industrial Chemistry, $6^{th}$, completely revised edition, Volume 38, Wiley-VCH, 2002). Additionally, KIP also may serve as important precursor of several carotenoids such as e.g. via the catalytic action of levodione reductase, whereby KIP is converted into the chiral intermediate (4R,6R)-4-hydroxy-2,2,6-trimethylcyclohexanone (actinol).

Unfortunately, the generation of TMHQ as known today is a time, material and cost intensive process which requires high temperatures and/or organic solvents, toxic heavy metal catalysts, with generation of undesired by-products.

Although the starting material α-IP is readily available, the known chemical conversion into KIP is a very ineffective process, with first isomerization of α-IP into β-IP followed by homogeneous liquid oxidation to KIP, a process with the equilibrium heavily shifted towards α-IP: no more than 2% of α-IP are converted into β-IP. Until now, there is no alternative, e.g. biocatalytic reaction, known which would lead to high yields of KIP via regioselective oxidation of α-IP.

Thus, there is a strong need to improve the known vitamin E synthesis, in particular to improve the production of KIP as one of the key-building blocks from its precursor, e.g. to reduce reaction and purification steps and/or to reduce waste and process energy demands, but in particular to improve the regioselectivity and total turnover numbers (TTN) of said reactions, especially in the oxidative conversion of α-IP to KIP.

Surprisingly, we now found a new biocatalytic route to KIP, i.e. a cascade system wherein KIP is generated from α-IP via a double allytic oxidation (FIG. 1A). Preferably, the first step is an enzymatic conversion using a heme containing oxidoreductase enzyme having cytochrome P450 enzyme activity followed by a second step, which might be also an enzymatic conversion, in particular via NADP(H) or NAD(H)-dependent enzymes, such as e.g. NADP(H) or NAD(H)-dependent oxidoreductases, or a chemical oxidation step as known to the person skilled in the art.

In particular, the present invention provides a two-step oxidation process, wherein in step 1 α-IP is converted to 4-hydroxy-α-isophorone (HIP) via biocatalytic action of a cytochrome P450 enzyme and wherein in step 2 said HIP is converted, i.e. oxidized, into KIP, said step 2 being either a chemical reaction or being catalyzed via action of a suitable enzyme. Preferably, both steps are performed as one-pot multi-enzymatic transformation reaction. With this approach, we were able to obtain conversion rates in the range of at least 60%, such as e.g. 70%, 80%, 90%, 95% or higher, i.e. up to 100% conversion.

Cytochrome P450 enzymes (CYPs or P450s) are a diverse superfamily of heme oxidoreductases capable of performing many oxidative reactions, most notably the insertion of oxygen into a chemically inert C-H bond, using oxygen as a benign oxidant and releasing water as by-product. During this catalytic cycle, oxygen activation is enabled by two electrons supplied by NAD(P)H and shuttled by redox partners. Direct aromatic ring hydroxylation is a synthetically attractive reaction which has been reported for several P450 enzymes. A well-known example of such P450 enzyme is the cytochrome P450 CYP102A1 from *Bacillus megaterium* commonly referred to as the P450 BM3. P450 BM3 is a water-soluble enzyme of 118 kDa. Until now, these enzymes have been hardly used in biotechnical processes, since they are difficult to express in the established host systems and are rather sensitive to inactivation in the isolated state.

The term "TTN", which is art-recognized, is defined as the ratio of product concentration and enzyme concentration calculated over 24 h, and is a determining feature of enzyme activity. TTN can be measured by HPLC, in particular through calibration curves (product formed) and CO difference spectroscopy (enzyme concentration). The method is known in the art. The improvement of the TTN values is one particular subject of the present application.

In one embodiment, the present invention provides a biological process for the conversion of α-IP to 4-hydroxy-α-isophorone (HIP), said conversion being catalyzed by an enzyme having P450 monooxygenase activity. Thus, α-IP is incubated in the presence of said enzyme under suitable conditions as defined herein for step 1.

Preferably, said biocatalytic conversion is the first part of a double oxidation cascade, wherein in step 1 α-IP is biocatalytic oxidized to (HIP), which is subsequently oxidized in step 2 (as defined below) into KIP.

As used herein, the terms "enzyme", "P450 monooxygenase", "cytochrome P450 monooxygenase" or "P450 enzyme" are used interchangeably herein in connection with the description of the present invention.

The enzyme used for step 1 may include any P450 monooxygenase including enzymes isolated from microorganisms, yeast or mammals. Preferably, the biocatalyst/enzyme is selected from the P450 monooxygenase of *Bacillus, Geobacillus, Pseudomonas, Erythrobacter, Burkholderia, Herpetosiphon, Ralstonia, Bradyrhizobium, Azorhizobium, Streptomyces, Rhodopseudomonas, Rhodococcus, Delftia, Saccharopolyspora, Comamonas, Burkholderia, Cupriavidus, Variovorax, Fusarium, Gibberella, Aspergillus* or *Amycolatopsis*, more preferably selected from *Bacillus megaterium, Bacillus subtilis, Bacillus licheniformis, Bacillus weihenstephanensis, Bacillus cereus, Bacillus*

*anthracis, Pseudomonas putida, Burkholderia* sp. 383, *Erythrobacter litoralis, Geobacillus* sp. Y412MC10, *Herpetosiphon aurantiacus, Ralstonia eutropha, Ralstonia pickettii, Ralstonia metallidurans, Bradyrhizobium japonicum, Azorhizobium caulinodans, Streptomyces avermitilis, Rhodopseudomonas palustris, Rhodococcus* sp., *Rhodococcus ruber, Rhodococcus* sp. NCIMB 9784, *Delftia acidovorans, Saccharopolyspora erythraea, Comamonas testosteroni, Burkholderia mallei, Cupriavidus taiwanensis, Variovorax paradoxus, Fusarium oxysporum, Gibberella zeae, Gibberella moniliformis, Aspergillus fumigatus* or *Amycolatopsis orientalis*, most preferably *Bacillus megaterium, Bacillus subtilis, Bacillus licheniformis, Bacillus weihenstephanensis, Bacillus cereus, Bacillus anthracis, Pseudomonas putida, Rhodococcus* sp., in particular *Bacillus megaterium* or *Bacillus subtilis*, such as *Bacillus megaterium* (P450 BM3, CYP102A1) shown in SEQ ID NO:1 or homologous sequences thereof showing the same enzymatic activity. Thus, the present invention is directed to a process as described herein wherein an enzyme having at least 35%, such as 40, 50, 60, 70, 75, 80, 85, 90, 95, 98, 99% identity to SEQ ID NO:1, the identity being determined over the entire amino acid sequence using ClustalW2 in the default settings of 24 Nov. 2009. An example of a useful mammalian enzyme is the human CYP2D6. Furthermore, preferred are chimeric enzymes of two or more P450 enzymes or at least domains of such enzymes, such as e.g. the heme domain from one enzyme and/or the NADPH-dependent reductase domain from another enzyme. A particular useful chimeric P450 enzyme is the self-sufficient P450cam-RhFRed P450 as shown in SEQ ID NO:3, encoded by a nucleic sequence including SEQID NO:4. Thus, the present invention is directed to a process as described herein wherein an enzyme having at least 62%, such as 70, 75, 80, 85, 90, 95, 98, 99% identity to SEQ ID NO:3, the identity being determined over the entire amino acid sequence of the reductase domain part RhFRed using ClustalW2 in the default settings of 24 Nov. 2009.

In one particular embodiment, step 1 according to the present invention is performed using the P450 BM3 (EC 1.6.2.4) as shown in SEQ ID NO:1, encoded e.g. by the nucleic acid sequence shown in SEQID NO:2.

In one particular embodiment of step 1 as defined herein, the chimeric self-sufficient P450cam-RhFRed enzyme is used consisting of the heme domain of the well-known CYP101A1 (P450cam, camphor 5-monooxygenase) from *Pseudomonas putida* fused to the NADPH-dependent reductase domain (RhFRed) of CYP116B2 from *Rhodococcus* sp. (P450RhF), see Robin et al., Beilstein J. Org. Chem. 2011, 7, 1494-1498 or O'Reilly et al., Catal. Sci. Technol. Catal Sci. Technol 2013, 3, 1490-1492.

A biocatalytic process of the present invention including e.g. step 1 and/or step 2 might be performed using either wild-type enzymes derivable from nature or modified or mutated, i.e. optimized, enzymes, such as modified or chimeric (i.e. "synthetic") P450 enzymes. Optimization also includes modification which enables high expression in a specific host system, which is a standard method and known in the art.

The term "wild-type" in the context of the present invention may include both P450 monooxygenase sequences derivable from nature as well as variants of synthetic (chimeric) P450 enzymes. The terms "wild-type P450" and "non-modified P450" are used interchangeably herein.

A "mutant", "mutant enzyme", "mutant P450 enzyme" or "P450 variant" such as P450 BM3 or P450cam-RhFRed modified enzyme, may include any variant derivable from a given wild-type or chimeric (in the sense as defined herein) enzyme/P450 (according to the above definition) according to the teachings of the present invention and being more active/efficient in e.g. regio-selectivity and/or TTN than the respective wild-type enzyme. For the scope of the present invention, it is not relevant how the mutant(s) is/are obtained; such mutants may be obtained, e.g., by site-directed mutagenesis, saturation mutagenesis, random mutagenesis/directed evolution, chemical or UV mutagenesis of entire cells/organisms, and other methods which are known in the art. These mutants may also be generated, e.g., by designing synthetic genes, and/or produced by in vitro (cell-free) translation. For testing of specific activity, mutants may be (over-)expressed by methods known to those skilled in the art. Different test assays are available, such as e.g. pNCA-assays, 4-AAP-assay or pNTP-assay which are all known to the skilled person. The terms "mutant P450 enzyme" and "modified P450 enzyme" are used interchangeably herein.

Thus, in one aspect the present invention is directed to a modified enzyme having P450 activity, in particular a P450 enzyme, showing—compared to the wild-type or non-modified enzyme—improved regio-enantioselectivity, improved enantiomeric excess values (ee) and/or improved TTN. Such mutation or modification is said to be a functional mutation.

Depending on the used enzyme in step 1, α-IP might be converted mainly into (R)-HIP, with e.g. an ee towards (R)-HIP (as compared to HIP) of at least 40%, such as at least 50%, 60%, 70%, 80%, 90%, 95%, 96%, 97%, 98% or even at least 99%. Step 1 as performed with a P450 mutant as defined herein might lead to an ee towards (R)-HIP of up to 99%.

The mutant P450 as according to the present invention are improved in the TTN, with preferred TTN in the range of at least 1 to 1.5 g/l/h, such as e.g. at least 2 g/l/h leading to a concentration of the reaction product in the range of 50 g/l after 24 h. More preferred are TTN values in the range of at least 10000 to 13000, such as e.g. at least 50000 to 100000. With regards to the improvement of TTN, the mutant P450 enzymes according to the present invention show an increase of at least 2-fold, such as at least 3, 4, 5, in particular at least 6-fold increase in TTN compared to the respective wild-type or non-modified P450 enzymes. This might be event increased by at least 10-fold.

The P450 enzyme used to generate the modified version according to one aspect of the present invention and which can be preferably used in the step 1 oxidation might be any P450 enzyme including chimeric forms, as long as the introduction of one or more mutations results in an improvement of regio-enantioselectivity, ee and/or TTN, i.e. improved bioconversion of α-IP into HIP-one intermediate generated in step 1 of the inventive process (see FIG. 1B). In particular, the modified P450 enzyme might be based on the wild-type P450 BM3 or P450cam-RhFRed, preferably the P450cam-RhFRed.

In a particular embodiment, the modified P450 enzyme produces at least 10 mmol/l corresponding to 1.5 g/l of HIP generated by biocatalytic oxygenation of α-IP. With regards to efficiency of conversion, step 1 of the bioconversion of α-IP to HIP using enzymes as described herein might be carried out with a conversion rate of at least about 60%, preferably at least about 70%, 75%, 80%, 90%, 95%, 98% conversion. As preferably step 2 is performed with the same conversion rates, more preferably a complete conversion from HIP to KIP, said conversion rates might apply to the complete double oxidation process, i.e. the cascade process from α-IP to KIP.

In one preferred embodiment, the at least one mutation is at one or more amino acid positions selected from the group consisting of amino acid positions corresponding to positions 87, 244, 247 and combinations thereof to the amino acid sequence of chimeric self-sufficient P450cam-RhFRed as shown in SEQ ID NO:3, defined as the wild-type sequence (this sequence already carries the amino acid substitution Y96F). More preferably, the wild-type P450cam-RhFRed is mutated wherein the mutated or modified enzyme comprises a mutation in one or more of the amino acid residues F87, L244 and/or V247 (in addition to Y96F which is already present in the parent or wild-type chimeric enzyme). Particularly preferred are amino acid substitutions but also other forms of mutations known to the skilled person are possible as long as they result in enzymes having improved properties as defined herein.

Preferably, the modified P450 enzyme such as the modified P450cam-RhFRed comprises amino acid substitutions on at least one position selected from F87, L244 and/or V247 shown in the wild-type chimeric enzyme (which already carries substitution Y96F).

With regards to preferred amino acid residues on position 244, the presence of a polar amino acid residue, e.g. asparagine, serine or cysteine or positively charged residues, e.g. histidine, leads to an improvement in ee and/or TTN values compared to L244 and according to the present invention. Preferably, the amino acid on position corresponding to position L244 in the wild-type chimeric P450cam-RhFRed shown in SEQ ID NO:3 is selected from alanine, asparagine, serine, glycine, isoleucine, cysteine, tyrosine or histidine, with the most preferred amino acid residue being adenine on position 244, e.g. substitution L244A.

With regards to preferred amino acid residues on position 247, the presence of an apolar side chain or the polar amino acid residue such as e.g. asparagine or serine leads to an improvement in ee and/or TTN values compared to V247 and according to the present invention. Preferably, the amino acid on position corresponding to position V247 in the wild-type chimeric P450cam-RhFRed shown in SEQ ID NO:3 is selected from lysine, phenylalanine, isoleucine or serine, with the most preferred amino acid residue being leucine on position 247, e.g. substitution being V247L.

With regards to preferred amino acid residues on position 87, there seem to be no preference for a specific amino acid leading to an improvement in step 1 of the inventive process. A preferred amino acid residue on position 87 is tryptophan, e.g. substitution F87W.

In one aspect, the mutated enzyme which might be used in step 1 is a modified P450 enzyme such as e.g. a modified P450cam-RhFRed comprising a combination of at least 2 mutations mentioned above, such as e.g. amino acid substitutions on positions corresponding to positions 244 and 247 in the wild-type chimeric P450cam-RhFRed according to SEQ ID NO:3, such as e.g. L244-V247 shown in SEQ ID NO:3, preferably a combination of substitutions is L244S-V247L, L244N-V247L, L244G-V247L, L244I-V247L, L244C-V247L, L244I-V247F, L244Y-V247F, L244N-V247F, L244H-V247F, L244G-V247F, L244I-V247I, L244I-V247S, or L244A-V247L, with most preferred being the combination L244A-V247L.

According to another aspect of the present invention, the mutated enzyme which might be used in step 1 is a modified P450 enzyme such as e.g. modified P450cam-RhFRed comprising a combination of at least 2 mutations mentioned above, such as e.g. amino acid substitutions on positions 244, 247 and 87, such as e.g. F87-L244-V247 shown in SEQ ID NO:3, preferably a combination of substitutions F87W-L244A-V247L, but also includes any of the above mentioned double amino acid substitutions on positions 244 and 247 in combination with preferably F87W.

The modified P450 enzyme according to step 1 of the present invention, such as e.g. modified chimeric P450cam-RhFRed, preferably comprises at least 1, at least 2 or at least 3 mutations, e.g. substitutions, on one of the above-identified positions when compared with the amino acid sequence of the corresponding non-modified chimeric enzyme as exemplified by SEQ ID NO:3. In case of amino acid substitutions on at least 3 of the herein-identified residues, preferably the combination of amino acid substitutions F87W-L244A-V247L, leading to an ee of 99% towards (R)-HIP from α-IP.

All these modifications mentioned above leading to a mutant P450 enzyme, in particular a mutant P450cam-RhFRed, might be used in a process for conversion, i.e. oxidation of α-IP into HIP, in particular for step 1 of the biocatalytic double oxidation, preferably one-pot biocatalytic double oxidation, as described herein.

The present invention features in one aspect nucleic acid sequences coding for the novel modified P450 enzymes as being part of the present invention as well as to vectors or systems used to express such modified enzymes in a suitable host system. The skilled person knows such vectors, hosts and the corresponding systems for expression of enzymes.

As used herein, the present invention also encompasses P450 enzymes with at least one of the abovementioned sequence positions, but additionally which carry amino acid substitution(s) other than the one mentioned specifically, but still lead to a mutant which, like the mutant which has been mentioned specifically, show the same properties with respect to the wild-type enzyme and catalyze at least one of the abovementioned hydroxylation reactions. Such mutations are also called "silent mutations", which do not alter the activity of the mutants as described herein.

The process as of step 1 cascade process as defined herein using mutant P450 enzymes according to the present invention, in particular the recombinant P450cam-RhFRed mutants, results in increased specific activity in the oxidation of α-IP resulting in HIP with improved TTN values and (enantio)selectivity for production of HIP from α-IP.

One particular aspect of the present invention is a two-step oxidation process, wherein step 1 as described above consisting of the conversion of α-IP to HIP using a heme containing oxidoreductase such as a P450 enzyme is followed by a subsequent oxidation, i.e. step 2 of the cascade oxidation as described herein. Step 2 might be a chemical oxidation known to the skilled person or, preferably, a further biocatalytic oxidation using a suitable enzyme for conversion of HIP into KIP (see FIGS. 1A and 1C).

In a preferred embodiment, step 2 according to the present invention is a biocatalytic conversion of HIP into KIP via the activity of a suitable enzyme, such as e.g. NADP(H) or NAD(P) dependent enzymes, including NADP(H) or NAD(P) dependent oxidoreductases (EC 1), preferably enzymes having activity as alcohol dehydrogenase, carbonyl reductase, keto reductase or monooxygenase, in particular alcohol dehydrogenase (ADH) or carbonyl reductase (CR) activity. More preferably, the enzyme is selected from ADH of *Candida magnoliae*, such as e.g. Cm-ADH10 (GenBank accession no. AGA42262.1), or carbonyl reductase from *Sporobolomyces salmonicolor* (UniProt accession no. Q9UUN9).

As used herein, the biocatalytic processes as of step 1 and/or step 2 can be carried out with either wild-type enzymes derivable from nature or modified or mutated, i.e.

optimized, enzymes. Step 1 and/or step 2 might be performed with isolated/purified enzymes or as a whole cell biocatalyst in a biotransformation reaction, wherein the enzyme(s) is/are expressed in a suitable host system as described herein.

With regards to the two-step process as defined herein, in one embodiment the biotransformation of step 1 followed by step 2 are carried out separately, i.e. not as a one-pot biocatalytic system. In this case, either step 1 and step 2 are running in the presence of suitable co-substrates added to the reaction, such as e.g. glucose, isopropanol or phosphite as suitable co-substrates for step 1, and/or e.g. acetone, chloroacetone, ethyl acetoacetate, ethyl levulinate, chloroacetone or ethyl acetoacetate, preferably chloroacetone or ethyl acetoacetate as suitable co-substrates for step 2. These co-substrates are combined with the enzymes used for step 1 and/or step 2 as defined herein.

Preferably, the co-substrates are present in an amount of at least 1 equivalent, more preferably in an amount of between 1 and 2 equivalents compared to the substrate, such as α-IP or HIP in the case of step 1 and step 2, respectively.

In one embodiment, the bioconversion or biotransformation or biocatalytic reaction (as interchangeably used herein) according to step 2 is carried out in the presence of an alcohol dehydrogenase, in particular ADH from *Candida magnoliae*, preferably Cm-ADH10 according to SEQ ID NO:5, which can be expressed from a nucleic acid sequence according to SEQ ID NO:6. Thus, HIP is incubated in the presence of said enzyme under suitable conditions as defined herein for step 2.

In a further embodiment, the bioconversion according to step 2 is carried out in the presence of a carbonyl reductase from *Sporobolomyces salmonicolor* (SSCR), in particular a carbonyl reductase according to SEQ ID NO:7, which can be expressed from a nucleic acid sequence according to SEQ ID NO:8.

The preferred enzyme to be used for step 2 is an ADH, more preferably Cm-ADH10, particularly in concentrations of about 0.5 to 1.5 mg/ml, preferably of about 1 mg/ml when used as purified enzyme.

In one aspect of the present invention there is provided a two-step oxidation process, wherein both steps are preferably catalyzed by suitable enzymes as described herein. Both enzymes or only one of the enzymes might be used in isolated, i.e. purified form. In a preferred double oxidation process according to the present invention, the process is performed as a biotransformation, wherein both enzymes to be used in step 1 and step 2 are present/expressed in a suitable host system. This double oxidation process might be carried out separately, i.e. the enzymes being expressed independently, or, which is preferred, the enzymes to be used in step 1 and step 2 are expressed in the same host and used as a one-pot reaction.

Expression of the enzymes used according to the present invention can be achieved in any host system, including (micro)organisms, which allows expression of the nucleic acids according to the invention, including functional equivalents or derivatives or mutants. Examples of suitable host (micro)organisms are bacteria, fungi, yeasts or plant or animal cells. Preferred organisms are bacteria such as those of the genera *Escherichia*, such as, for example, *Escherichia coli*, *Streptomyces*, *Bacillus*, *Rhodococcus*, such as for example *Rhodococcus erythropolis*, *Rhodococcus rhodochrous*, *Rhodococcus ruber*, *Rhodococcus equi*, or *Pseudomonas*, such as for example *Pseudomonas putida*, or eukaryotic microorganisms such as *Saccharomyces*, such as *Saccharomyces cerevisiae*, *Aspergillus*, such as *Aspergillus niger*, *Pichia*, such as *Pichia pastoris*, *Hansenula*, such as *Hansenula polymorpha* or *Yarrowia*, such as *Yarrowia lipolytica* and higher eukaryotic cells from animals or plants. In particularly preferred is *Escherichia*, *Bacillus*, *Pseudomonas* or *Rhodococcus*, more particularly preferred is *Escherichia coli* B, such as *E. coli* BL21 (DE3) or other derivatives, or *E. coli* K-12 strains.

Independently of the expression in a one pot or two pot system, the biotransformation of step 1 and/or step 2 as defined herein is particularly performed at a temperature in the range of from 10° C. to 50° C., preferably between 20° C. and 40° C., such as e.g. about 30° C. to 40° C.

As used herein, and independently of the expression in a one pot or two pot system, the biotransformation of step 1 and/or step 2 as defined herein is in particular performed at a pH of from 4.0 to 10.0, preferably of from 5.7 to 8.0, in particular of from 7.0 to 8.0.

As used herein, and independently of the expression in a one pot or two pot system, the biotransformation of step 1 and/or step 2 as defined herein is particularly performed in a buffer selected from phosphate, such as potassium carbonate, acetate or Tris-HCl. The skilled person will know which buffer is most suitable with regards to the used enzymes.

As used herein, a process according to the present invention—and in particular step 1—is performed in the presence of preferably 2 to 6 µM P450 enzyme, either the wild-type enzyme or the mutants as defined herein. With regards to step 2 of the present invention, the concentration of enzyme, such as e.g. ADH, preferably Cm-ADH10, the concentration may vary. Optionally, the one pot reaction might be carried out in the presence of 10 mg/ml glucose as co-substrate with optional addition of co-factors such as NADP(H) or NAD(H).

Typically, a process according to the present invention including step 1 and step 2 and independently of the expression in a one pot or two pot system, runs between 1 h up to 48 h, preferably in the range of from 18 h to 24 h.

Thus according to one embodiment, the present invention relates to a biocatalytic process for the conversion of α-isophorone to 4-hydroxy-α-isophorone (HIP), wherein α-isophorone is incubated under suitable conditions in the presence of a heme containing oxidoreductase, preferably an enzyme having P450 monooxygenase activity, more preferably selected from P450cam-RhFRed or *Bacillus megaterium*, even more preferably a polypeptide according to a sequence having at least 35% identity to SEQ ID NO:1 or a sequence with at least 62% identity to SEQ ID NO:3, said suitable conditions include incubation at pH of from 4.0 to 10.0 for 1 to 48 h with optionally isolation of HIP from the reaction mixture.

Thus, according to a further embodiment, the present invention relates to a biocatalytic process for the production of ketoisophorone (KIP), wherein the product from step 2 is incubated under suitable conditions in the in the presence of a NAD(H) or NADP(H)-dependent enzyme, preferably NAD(H) or NADP(H)-dependent oxidoreductase (EC 1), more preferably an enzyme having activity as alcohol dehydrogenase, carbonyl reductase, keto reductase or monooxygenase, even more preferably having alcohol dehydrogenase or carbonyl reductase activity, most preferably an alcohol dehydrogenase from *Candida magnoliae* or a carbonyl reductase from *Sporobolomyces salmonicolor*, said suitable conditions include incubation at pH of from 4.0 to 10.0 for 1 to 48 h with optionally isolation of KIP from the reaction mixture.

As used herein, the terms "one-pot" means that the process as described herein including step 1 and step 2 is carried out in the same reactor (i.e. the same reaction buffer under the same conditions), i.e. there is only one reaction comprising 2 steps. The "same reactor" is defined as only the same reaction "pot" and/or the same host organism. It might furthermore mean that the polynucleotides encoding both enzymes to be used in step 1 and step 2 are cloned on the same vector or are both integrated in the genome of the (same) host organism. In this case, the process is preferably carried out as simultaneous single-step process as defined below.

The term "double oxidation", "double allylic oxidation", "cascade oxidation", "double oxidation cascade" are used herein interchangeable and describe two oxidation steps, leading to conversion of α-IP to HIP, i.e. step 1 as defined herein, and further to KIP, i.e. step 2 as defined herein (see FIG. 1A). These 2 oxidations might be performed simultaneously, i.e. might occur at the same time, which would be defined also defined as "one-step process", or might be subsequently, i.e. step 1 is followed by step 2 (either in a one-pot or two-pot system as defined above), which would be defined as "two-step process", which is the preferred method.

The term "HIP" as used herein includes both enantiomers in any possible ratio, i.e. mixtures of either (R)- and (S)-HIP as well as the single enantiomers, without any enantiomeric preference with regards to the present invention. Depending on the P450 enzyme, an ee towards either (R)- or (S)-HIP might be generated. For example, use of the mutant P450 in step 1 as described herein leads to an ee of up to 99% towards (R)-HIP. In case step 1 would be performed in the presence of P450 BM3 this preference towards (R)-HIP would be less prominent, such as e.g. in the range of about 80% or less. The HIP obtained via step 1 is further converted into KIP in the presence of an enzyme as defined herein, wherein said enzyme is capable of using HIP as defined herein as substrate (and optionally further co-substrates or co-factors), including a substrate which is selected from (R)-HIP, (S)-HIP, or a mixture of (R)/(S)-HIP, including mixtures with an ee in the range of 50, 60, 70, 80, 90, 95, 98, 99% towards (R)-HIP.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in μmol substrate consumed or product formed per min per mg of protein. Typically, μmol/min is abbreviated by U (=unit). Therefore, the unit definitions for specific activity of μmol/min/(mg of protein) or U/(mg of protein) are used interchangeably throughout this document.

The term "vitamin E" is used herein as a generic descriptor for all tocopherol and tocotrienol derivatives exhibiting qualitatively the biological activity of α-tocopherol (IUPAC-IUB Recommendation 1981, Eur. J. Biochem. 123, 473-475, 1982).

In connection with the present invention it is understood that the mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM). This applies e.g. to *Sporobolomyces salmonicolor*, which is also known under the synonym (and as used interchangeably herein) *Sporidiobolus salmonicolor*.

The present invention includes the following non-limiting embodiments:

(1) A biocatalytic process for the conversion of α-isophorone to 4-hydroxy-α-isophorone (HIP), wherein α-isophorone is incubated under suitable conditions in the presence of a heme containing oxidoreductase, preferably an enzyme having P450 monooxygenase activity, more preferably selected from P450cam-RhFRed or *Bacillus megaterium*, even more preferably a polypeptide according to a sequence having at least 35% identity to SEQ ID NO:1 or a sequence with at least 62% identity to SEQ ID NO:3, said suitable conditions include incubation at pH of from 4.0 to 10.0 for 1 to 48 h with optionally isolation of HIP from the reaction mixture.

(2) A biocatalytic process for the production of ketoisophorone (KIP), wherein the product from step 2 is incubated under suitable conditions in the in the presence of a NAD(H) or NADP(H)-dependent enzyme, preferably NAD(H) or NADP(H)-dependent oxidoreductase (EC 1), more preferably an enzyme having activity as alcohol dehydrogenase, carbonyl reductase, keto reductase or monooxygenase, even more preferably having alcohol dehydrogenase or carbonyl reductase activity, most preferably an alcohol dehydrogenase from *Candida magnoliae* or a carbonyl reductase from *Sporobolomyces salmonicolor*, said suitable conditions include incubation at pH of from 4.0 to 10.0 for 1 to 48 h with optionally isolation of KIP from the reaction mixture.

(3) A process for the conversion of α-isophorone into KIP, wherein the process of embodiment (1) is followed by the process of embodiment (2).

(4) A process according to any of the embodiments (1), (2) or (3), wherein the biocatalytic process for the conversion of α-isophorone to 4-hydroxy-α-isophorone (HIP) and/or the conversion of HIP to ketoisophorone (KIP) is carried out in the presence of (a) a co-substrate selected from the group consisting of glucose, isopropanol and phosphite with regards to conversion of α-isophorone to HIP; or (b) a co-substrate selected from the group consisting of acetone, chloroacetone, ethyl acetoacetate, ethyl levulinate, chloroacetone and ethyl acetoacetate with regards to conversion of HIP to KIP.

(5) A process for the conversion of α-isophorone into KIP, wherein the process of embodiment (1) is followed by a chemical conversion of HIP into KIP.

(6) A process according to any of the embodiments (1), (2), (3) or (4), wherein the process is performed in a one-pot biocatalytic system.

(7) A process according to any of the embodiments (1), (2), (3), (4), (5) or (6), wherein the conversion rate is at least 60%.

(8) A modified P450 monooxygenase capable of regio- and stereoselective hydroxylation of α-isophorone into HIP, wherein the amino acid sequence comprises one or more mutation(s) on a position corresponding to position(s) 96, 87, 244, 247, and/or combinations thereof of a P450cam-RhFRed P450 monooxygenase according to SEQ ID NO:3, and wherein the total turnover number is increased by at least 2-fold compared to the respective non-modified P450 monooxygenase.

(9) A modified P450 monooxygenase according to embodiment (8), wherein:

(a) the introduced amino acid on a position corresponding to position 244 are selected from the group consisting of alanine, asparagine, serine, glycine, isoleucine, cysteine, tyrosine and histidine, preferably from alanine; and/or (b) the introduced amino acid on a position corresponding to position 247 are selected from the group consisting of lysine, phenylalanine, isoleucine and serine, preferably from lysine; and/or (c) the introduced amino acid on a position corresponding to position 87 is tryptophan; and/or (d) the introduced amino acid on a position corresponding to position 97 is phenylalanine.

(10) A biocatalytic process according to any of embodiments (1), (2), (3), (4) (5), (6) or (7), wherein the conversion of α-isophorone to HIP is carried out with a modified P450 monooxygenase according to embodiments (8) or (9).

(11) A polynucleotide sequence sequence comprising a DNA sequence coding for a P450 monooxygenase as of embodiments (8) or (9).

(12) A host cell wherein a P450 monooxygenase according to embodiments (8) or (9) is expressed, preferably the host being selected from the group consisting of bacteria, fungi, yeasts or plant or animal cells, more preferably selected from *Escherichia, Streptomyces, Bacillus, Rhodococcus, Pseudomonas, Saccharomyces, Aspergillus, Pichia, Hansenula* or *Yarrowia*, even more preferably selected from *Escherichia coli, Rhodococcus erythropolis, Rhodococcus rhodochrous, Rhodococcus ruber, Rhodococcus equi, Pseudomonas putida, Saccharomyces cerevisiae, Aspergillus niger, Pichia pastoris, Hansenula polymorpha* or *Yarrowia lipolytica*, most preferably selected from *Escherichia coli* B, in particular *E. coli* BL21 (DE3) or other derivatives or *E. coli* K-12.

(13) A process for the production of vitamin E, comprising the step of biocatalytic conversion of α-isophorone into KIP according to any of embodiments (2), (3) or (4).

(14) A process according to embodiment (13), wherein the biocatalytic conversion of α-isophorone into KIP is performed as one-pot two-step process.

The present invention is now described in greater detail with reference to FIGS. 1 to 9 and the following examples. The work leading to this invention has received funding from the European Union (EU) project ROBOX (grant agreement n° 635734) under EU's Horizon 2020 Programme Research and Innovation actions H2020-LEIT BIO-2014-1.

FIG. 1: FIG. 1A shows the proposed one-pot double allylic oxidation, wherein α-isophorone (α-IP, 1) is in a first step oxidized via enzymatic action of a cytochrome P450 enzyme (P450) leading to 4-hydroxy-α-isophorone (HIP, 6), which might be further oxidized via enzymatic action of aldehyde dehydrogenase (ADH) to 2,6,6-trimethylcyclohex-2-ene-1,4-dione (KIP, 3). For further explanation see in the text. Possible products of the P450 oxidation of α-IP (1) are HIP (6), HIMP (7) and IPO (8) shown in FIG. 1B. The regeneration of CM-ADH10 catalyzing the oxidation from (R)-HIP to KIP using different co-substrates such as acetone (9a), chloroacetone (9b), ethyl acetoacetate (9c) and ethyl levulinate (9d) leading to the respective reduction products 10a-d, wherein "R" defines the respective substituent to result in the different co-substrates 9a-d is shown in FIG. 1C. Whole-cell double oxidation cascade of α-IP to KIP using *E. coli* co-expressing P450-WAL and Cm-ADH10 is shown in FIG. 1D. For more explanation, see text.

Figure 2:
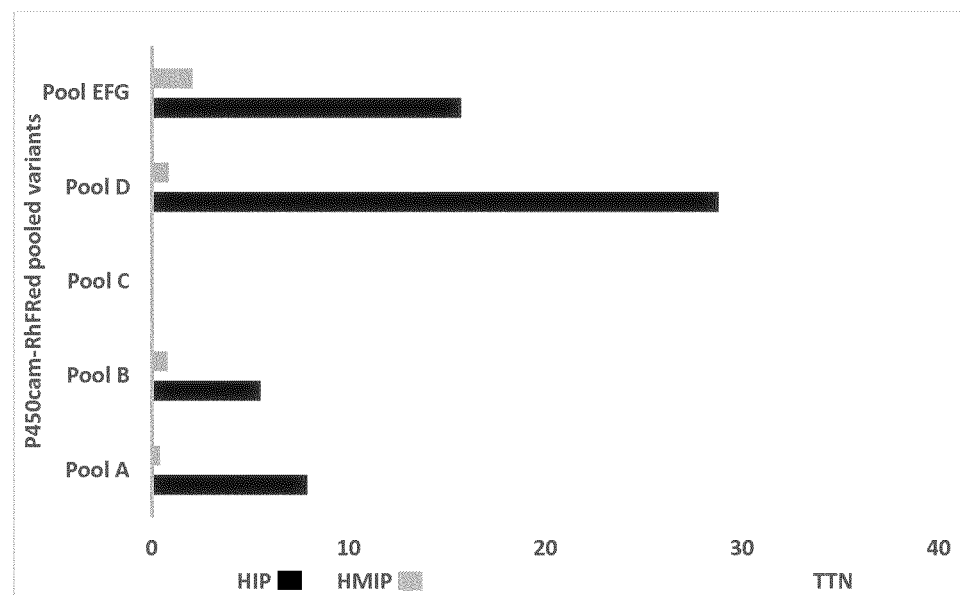

FIG. 2: Comparison of TTN as shown of the x-axis for HIP (black bars) and HMIP (grey bars) obtained for P450cam-RhFRed pooled variants shown on the y-axis. For further explanation see in the text.

Figure 3:
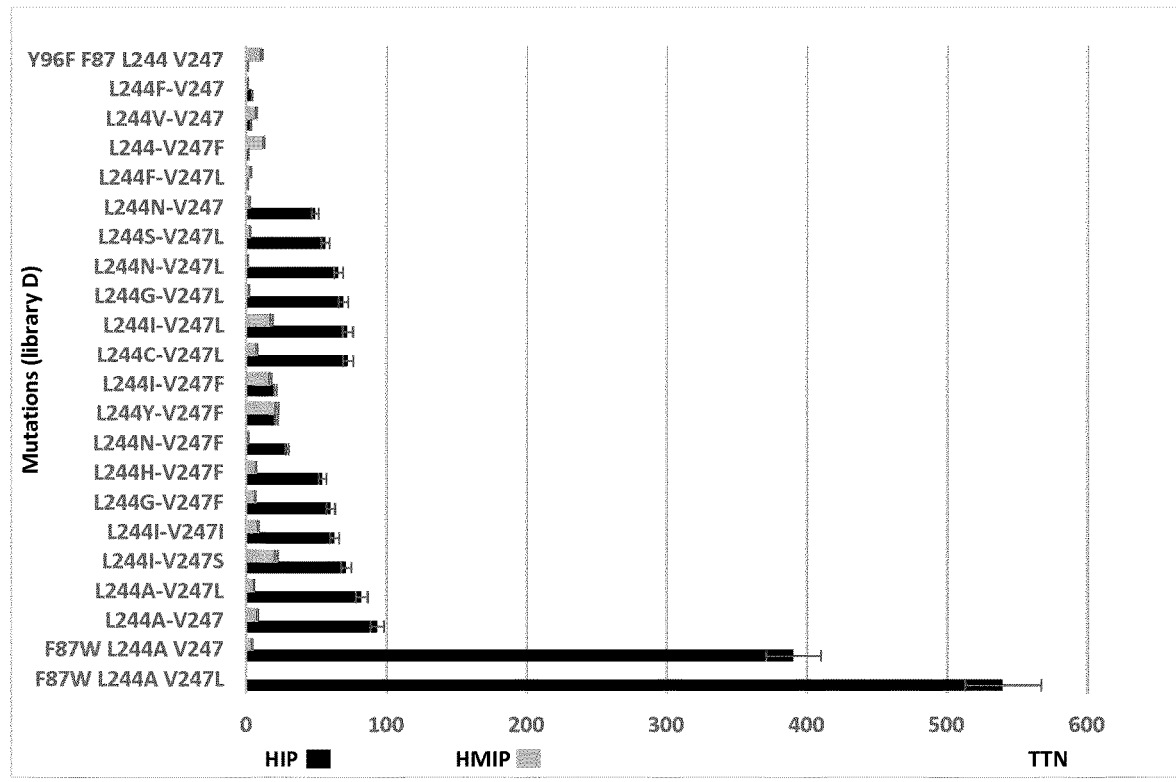

FIG. 3: Comparison of TTN as shown of the x-axis for HIP (black bars) and HMIP (grey bars) obtained for library D (mutated locations) shown on the y-axis. The data is based on the wild-type P450cam-RhFRed carrying the substitution Y96F. The introduction of F87W in said background together with L244A-V247L led to more than a 6-fold improvement of the TTN values with respect to L244A-V247L mutant. For further explanation see in the text.

Figure 4:
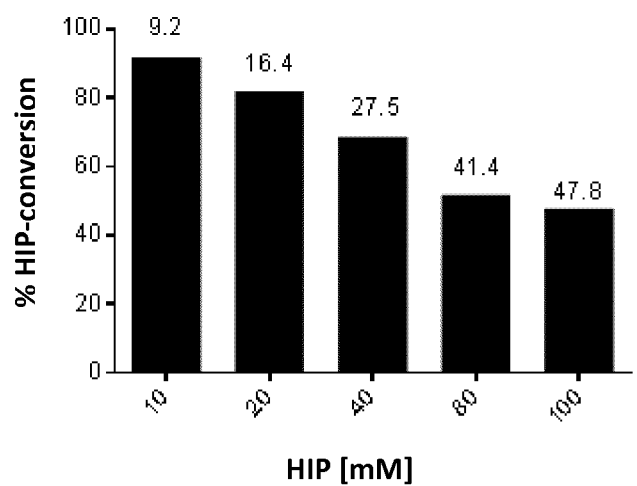
Figure 5:
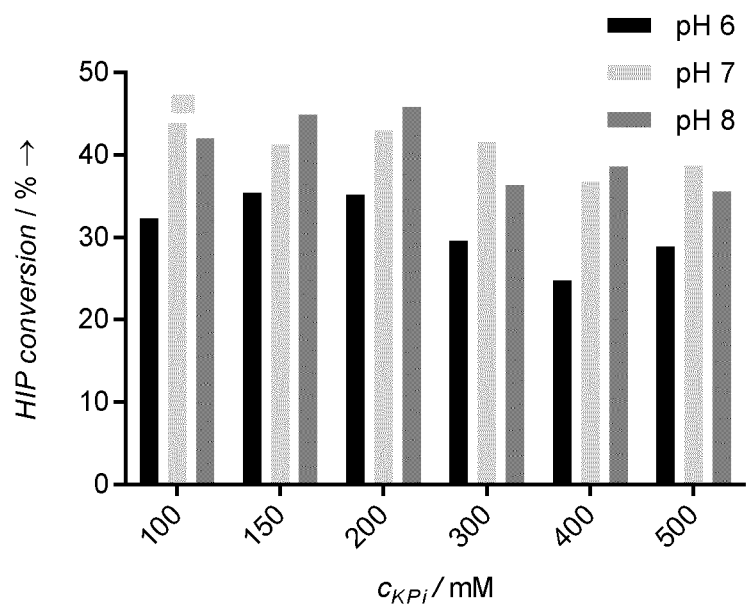
Figure 5:
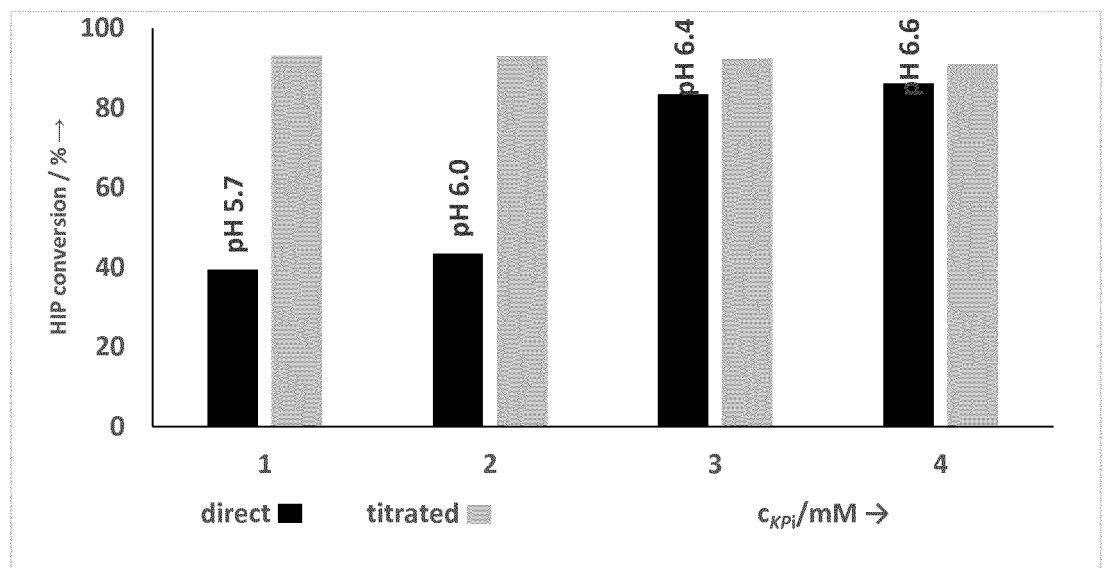

FIG. 4: Bar chart showing conversion values obtained with different HIP concentration. Reaction set-up: 1 mg/mL purified Cm-ADH10, 0.25 mM NADP+ and 0.5% v/v ethyl acetoacetate as co-substrate for cofactor regeneration (30° C., 24 h). Product concentrations (mM) are given above each bar. Conversion of HIP in % is shown on the y-axis, HIP concentration in mM is shown on the x-axis. For further explanation see in the text.

FIG. 5A: Effect of buffer concentration and pH on Cm-ADH10 activity. Reaction set-up: 1 mg/mL purified Cm-ADH10, 0.25 mM NADP+ and 0.5% v/v ethyl acetoacetate as co-substrate for cofactor regeneration (30° C., 4.5 h). For further explanation see in the text.

FIG. 5B: Effect of the pH reached after the P450-catalyzed reaction on Cm-ADH10 performance. $KP_i$ buffer concentration used in the first step is given on the x-axis ("1"=50+100 mM KCl; "2"=100 mM; "3"=200 mM; "4"=300 mM). Black bars: HIP conversion after direct addition of Cm-ADH10 (the pH measured after the first step is indicated above). Grey bars: HIP conversion when the supernatant of the first reaction was titrated to pH 8.0 before Cm-ADH10 addition. For more explanation, see text.

Figure 6:
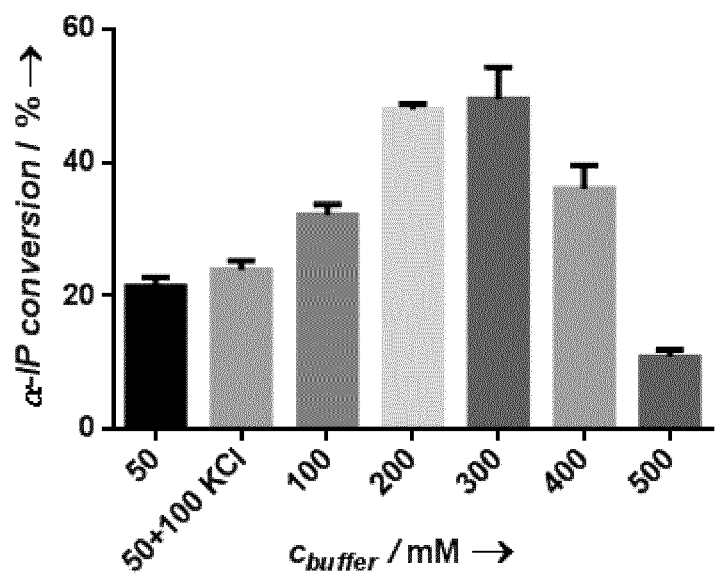
Figure 6:
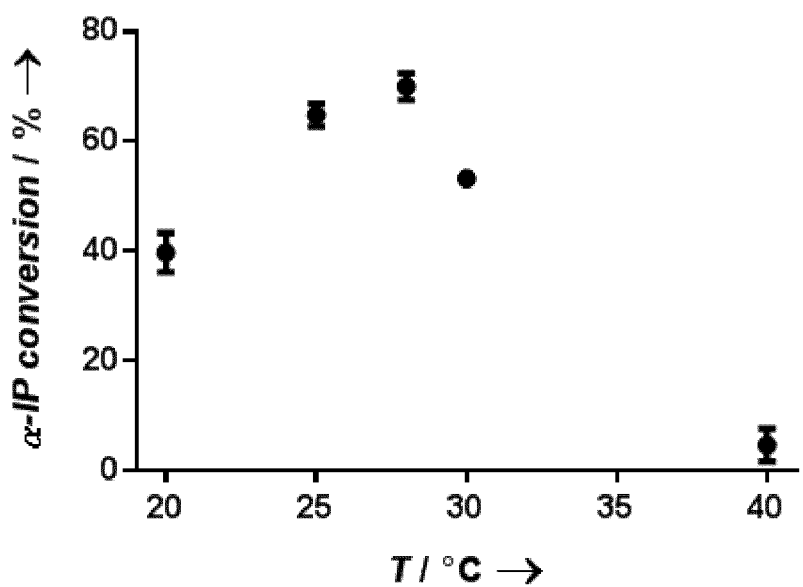

FIG. 6: Optimization of the allylic oxidation of α-IP catalyzed by P450cam-RhFRed-WAL. FIG. 6A shows the effect of buffer concentration. Reaction set-up: 200 mg mL$^{-1}$ wet cells resuspended in KPi buffer pH 8.0 (concentration given on the x-axis), 10 mg mL$^{-1}$ glucose, 20 mM α-IP, 2% DMSO, 20° C., 1 mL final volume in deep-well plate, 24 h reaction time. FIG. 6B shows effect of temperature. Reaction set-up: same as above, exception being the buffer adopted (200 mM $KP_i$, pH 8.0) and substrate concentration (15 mM) The x-axis shows the temperature (up to 40° C.), the y-axis shows α-IP conversion in %.

Figure 7:
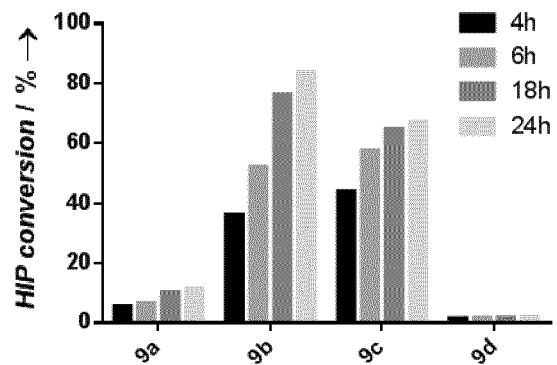
Figure 7:
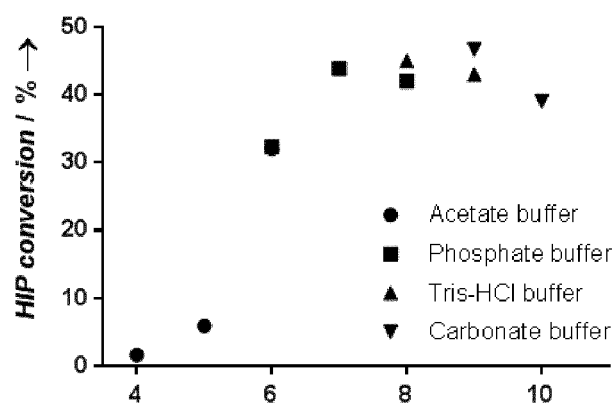
Figure 7:
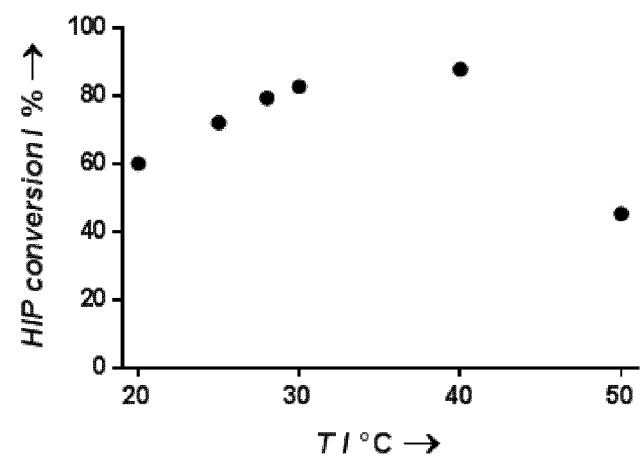

FIG. 7: Optimization of the oxidation of (R)-HIP catalyzed by Cm-ADH10. The y-axis shows HIP conversion in %. FIG. 7A shows the effect of different co-substrates. Reaction set up: 100 mM KPi buffer pH 7.5, 1 mg mL$^{-1}$ Cm-ADH10, 0.25 mM NADP+, 0.5% v/v co-substrate, 40 mM (R)-HIP, 30° C. FIG. 7B shows the effect of pH as indicated on the x-axis. Reaction set up: 100 mM indicated buffer, 1 mg mL–1 Cm-ADH10, 0.25 mM NADP+, 0.5% v/v chloroacetone, 40 mM (R)-HIP, 30° C., 4 h. FIG. 7C shows the effect of temperature as indicated in ° C. on the x-axis. Reaction set up: 200 mM KPi buffer pH 8.0, 1 mg mL–1 Cm-ADH10, 0.25 mM NADP+, 0.5% v/v co-substrate, 40 mM (R)-HIP, 24 h. For further details see text or FIG. 1C.

Figure 8:
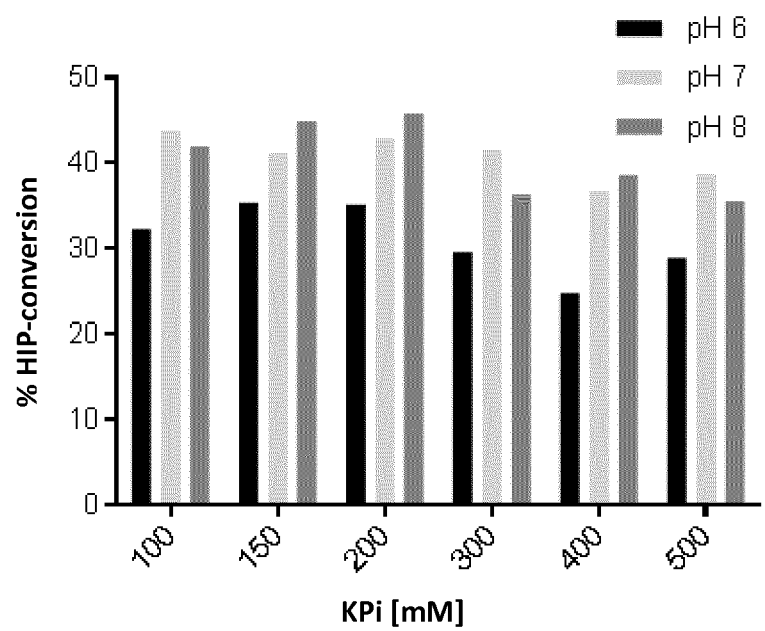

FIG. 8: Effect of buffer concentration and pH on Cm-ADH10 activity. Reaction set-up: 1 mg/mL purified Cm-ADH10, 0.25 mM NADP+ and 0.5% v/v ethyl acetoacetate as co-substrate for cofactor regeneration (30° C., 4.5 h). HIP-conversion in % is shown on the y-axis, the concentration of KPi buffer in mM is shown on the x-axis.

Figure 9:
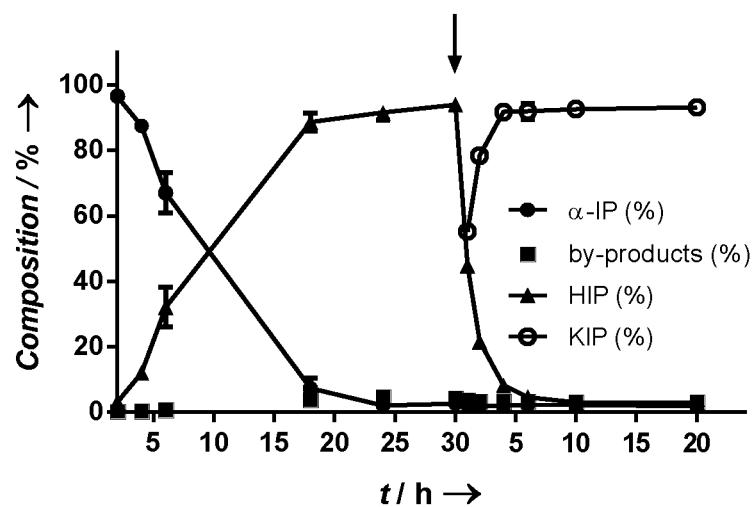

FIG. 9: Time-course experiment for the one-pot two-step double allylic oxidation of α-IP. Reaction set up: 200 mg mL$^{-1}$ wet cells resuspended in 200 mM KPi buffer pH 8.0, 10 mg mL$^{-1}$ glucose, 10 mM α-IP, 2% DMSO (first step, 28°

C.), then addition of 20% v/v Cm-ADH10 cell-free extract and 1.6 eq. of chloroacetone to the supernatant of the first reaction (second step, 40° C.). The arrow indicates the time of addition. Composition in % is shown on the y-axis, Times per h is shown on the x-axis.

EXAMPLE 1: GENERAL METHODOLOGY

All chemicals solvents, and carbon monoxide for CO difference spectroscopy used were of analytical grade and purchased from Sigma Aldrich (Poole, Dorset, UK) or BOC gases (Guildford, UK). Competent cells and enzymes were received from New England Biolabs (NEB). M9 minimal salts (5×) were purchased from Sigma-Aldrich, reconstituted by stirring the recommended amount of powder in water and sterilized by autoclaving. 40% glucose (w/v), antibiotics 1000×, 1 M $MgSO_4$, 1 M $CaCl_2$), and 25% (w/v) $FeCL_3$ were prepared in $dH_2O$ and filter sterilized through a 0.2 μm syringe filter.

Inverse PCR reactions carried out using Eppendorf Mastercycler Gradient thermal cyclers according to NEB guidelines, followed by DpnI digestion before carrying out ligation reaction for 1 h at 25° C. with T4 DNA ligase and polynucleotide kinase, according to the manufacturers instruction. NEB 5-alpha competent *E. coli* (high efficiency) were then transformed according to the manufacturer instruction and sequence verified by plasmid sequencing. Expression plasmids were generated by standard restriction cloning. P450cam-RhFRed site-directed mutants were made starting from variants in the previously developed libraries (see Example 2) using the appropriate primers shown in Table 1. Primer synthesis and DNA sequencing were performed by Eurofins Genomics. An Avril restriction site was added to P450cam-RhFRed by PCR using the primers "T7 for modified" and "AvrII rev" and the sequence cloned in pCDF-1b using NcoI and Avril restriction sites. For the two-vector strategy for coexpression (or ADHs expression trials), SSCR and Cm-ADH10 were cloned into pET28a vector, using NdeI and XhoI restriction sites that were introduced by PR using primers "NdeI Sporo for" and "XhoI Sporo rev" or "NdeI ADH10 for and "XhoI ADH10 rev", respectively. Plasmid carrying genes encoding for the selected ADHs were kindly provided by c-LEcta GmbH, Leipzig, Germany.

TABLE 1.

Oligonucleotides used for inverse PCR reactions. Mismatching bases are underlined.

| Primer | Primer sequence 5'-3' | SEQ ID NO: |
|---|---|---|
| F87W for, Tm = 57° C. | GAGTGCCCGTGGA TCCCTCGTGaaGC | 9 |
| F87W rev, Tm = 57° C. | GCTGGAAAAGT GGCGGTAATC | 10 |
| L244A for, Tm = 59° C. | AGGATGTGTGGCGC GTTACTGGTCGGC | 11 |
| L244A rev, Tm = 61° C. | CTTGGCTTCGTCA CTGGTGATCG | 12 |
| L244A-V247L for, Tm = 63° C. | AGGATGTGTGGCGCG TTACTGCTCGGCGGC CTGGATAC | 13 |
| AvrII rev, Tm = 65° C. | TAGTCTCCTAGGTCAG AGTCGCAGGGCCAGCc | 14 |
| AflII rev, Tm = 65° C. | TCGTCTCTTAAGTCAG AGTCGCAGGGCCAGCC | 15 |
| T7 for modified, Tm = 62° C. | TAATACGACTCACTAT AGGGAGACCACAACGG | 16 |
| NdeI ADH10 for, Tm = 63° C. | ACGTAGCATATGACGA CTACTTCAAACGCGCT TGTC | 17 |
| NcoI CmADH for, Tm = 63° C. | ATGCTACCATGGGGAT GACGACTACTTCAAAC GCGCTTGTC | 18 |
| AflII CmADH rev, Tm = 60° C. | ATGTATCTTAAGCAAT CAAGCCATTGTCGACC AC | 19 |
| XhoI ADH10 rev, Tm = 60° C. | ACGTCACTCGAGTTAA GCAATCAAGCCATTGT CGACCAC | 20 |
| AvrII ADH10 rev, Tm = 60° C. | AGTCAGCCTAGGTTAA GCAATCAAGCCATTGT CGACCAC | 21 |
| NdeI Sporo for, Tm = 60° C. | CTGGATCATATGGCCAA AATCGATAATGCCGTG | 22 |
| XhoI Sporo rev, Tm = 61° C. | TGCATGCTCGAGTTAG GCTGTTTCGCTACCAA CCAGG | 23 |

Chiral normal HPLC for measurement of enzymatic activity was carried out on an Agilent System (Santa Clara, CA, USA) equipped with a G4225A degasser, G1311A quaternary pump, a G1329A well plate autosampler unit, a G1315B diode array detector and a G1316A thermostatted column compartment. Separation of (S)- and (R)-HIP was carried out using a CHIRALPAK® AS-H column (5 μm particle size, 4.6 mm diameter×250 mm; Daicel Chemical Industries Ltd) operating in isocratic mode with 80% hexane and 20% isopropanol for 18 min at 25C. Injection volume was 5μL and chromatograms were monitored at 254 nm. Retention times were as follow: KIP 9.5 min, (S)-HIP 10.9 min α-IP 12.4, (R)-HIP 13.3 min. Automated GC analysis was performed on an Agilent 6850 GC (Agilent, Santa Clara, CA, USA) with a flame ionization detector (FID) equipped with an Agilent HP-1 column (30 m length, 0.32 mm inner diameter, 0.25 μm film thickness, Agilent, Santa Clara, CA, USA). 2 μL of property diluted sample was injected at a split ratio 10:1. The inlet temperature was set at 200° C., detector temperature at 250° C. and pressure maintained at 6.8 psi. The following method was applied: initial temperature 50° C.; 10° C./min to 220, hold 2 min. The corresponding retention times were: α-IP 7.4 min, KIP 7.6, possible KIP-reduction by-product 7.8 min and HIP 9.7 min. Calibration curves of decane vs 6 or 3 were constructed in order to calculate TTNs or conversion values, respectively.

Protein activity measurement of the P450 BM3 mutant libraries is described in more details in Examples 1 of WO2013160365. The wild-type P450 BM3 is shown in SEQ ID NO:3, with the encoding nucleic acid sequence shown in SEQ ID NO:4.

Whole cell P450 concentration measurement was performed on a plate reader (Tecan Infinite 200 series, Männedorf, CH) according to Kelly et al. (Beilstein J. Org. Chem. 2015, 11, 1713-1720) and for cell lysates on a Cary 50 UV/Visible spectrophotometer (Agilent Technologies, Santa Clara, CA, USA) according to the protocol by Omura and Sato (J. Biol. Chem. 1964, 239, 2370-2378). NMR spectra were recorded on a Bruker Avance 400 spectrometer (400.1 MHz for 1H and 100.6 MHz for 13C) in deuterated chloroform.

Preparation of (R)-HIP and (S)-HIP were prepared according to Hennig et. al. (Tetrahedron: Asymmetry 2000, 11, 1849-1858). Benzeneruthenium(II) chloride dimer (10.5 mg) and (1S,2R)-2-Amino-1,2-diphenylethanol (17.7 mg) were dissolved in 5 mL of isopropanol and the red solution stirred for 30 min at 80° C. Afterwards, 36.5 mL of isopropanol were added and the solution cooled to 28° C. Then, ketoisophorone (631.6 µL) and NaOH (2 mL, 0.1 M in isopropanol) were added to give a darker solution and the reaction followed until completion (ca. 3 hours). The reaction mixture was then filtered through Celite and the filtrate evaporated to afford a black oily residue. The product (S)-HIP was then purified by silica gel chromatography. The column was successively eluted with cyclohexane containing 20, 50 and 70% ethyl acetate and then solvents evaporated to afford a dark green oily residue (253.4 mg, 40% isolated yield). For the preparation of (R)-HIP, the same procedure was followed, but (1R,2)-2-Amino-1,2-diphenylethanol was used.

Expression and purification of proteins was as follows: plasmids (pET-14b, pCDF-1b or pET-28a) carrying genes encoding P450cam-RhFRed variants were stored at 4° C. Chemically competent E. coli BL21 (DE3) cells were transformed by heat shock according to manufacturer instructions. Transformants were plated on LB agar with added antibiotic (150 µg/ml ampicillin or 50 µg/ml for spectinomycin and kanamycin) and grown at 37° C. for 16 hours. Single colonies were picked from plates to prepare starter cultures in LB medium supplemented with antibiotic. After 16 hours, expression cultures were inoculated 1/100 using LB starter cultures and, to guarantee proper aeration, cultures volume was no more than 25% of the total conical flask volume. P450 expression in minimal medium was carried out according to Kelly et al. (supra): 1×M9 salts solution were supplemented with 0.4% glucose, 0.05% of $FeCl_3$, 1 mM $MgSO_4$, 1 mM $CaCl_2$) and cells were grown with vigorous shaking (200 rpm) at 37° C. until an OD600 of 0.8 was reached. At this stage, isopropyl β-D-1-thiogalactopyranoside (IPTG, 0.4 mM) was added to induce protein expression, along with ALA (0.5 mM) supplementation. Protein expression was carried out at 20° C. with shaking at 200 rpm for 20 h. The use of complex media (e.g., LB, TB and auto-induction media) resulted in the expression of the protein in the insoluble fraction or soluble inactive protein (data not shown).

Similarly, production of Cm-ADH10 and SSCR was carried out following a protocol similar to that for P450cam-RhFRed expression, the exception being the medium used (TB instead of M9) and the need for 5-ALA supplementation (not added). SDS-polyacrylamide gel electrophoresis (SDS-PAGE) was employed to confirm protein expression. Recombinant Cm-ADH10 was obtained by inoculating 1 L of Terrific broth containing 50 µg/mL kanamycin with transformed cell E. coli BL21 (DE3) and incubated until an OD600 of 0.6; protein production was induced with 0.4 mM IPTG at 20° C. and production was kept for 16 h. Cells were harvested by centrifugation (2831 g, 20 min, 4° C.) and kept at −80° C. until purification. Cells from 1 L of culture were suspended in 50 mL of 20 mM Tris·HCl, pH 7.5. The crude extract was prepared by sonication 5 min, 70% amplitude, 5 s on/off. Cell debris was removed by ultracentrifugation at 31,000 g for 45 min, 4° C. The supernatant was filtrated using a 0.45 um filter. The cell-free extract was applied to a 5 mL HisTrap FF column using an ÄKTA Pure (GE healthcare) at 1 ml/min at 4° C. and a 20 mM imidazole solution in 20 mM Tris·HCl buffer, pH 7.5. The column was washed with 4-6 CV of a 50 mM imidazole solution in 20 mM Tris·HC buffer, pH 7.5. Pure enzyme was eluted using 3 CV of a 500 mM imidazole solution in 20 mM Tris·HC buffer, pH 7.5. Enzyme was concentrated and excess of imidazole was removed with a concentrator Amicon® Ultra concentrator (10,000 NMWL; Millipore) at 4000 g. Typically, the enzyme was diluted to 10 mg/mL in 50 mM KPi buffer (pH 7.5) to carry out biotransformation trials and kinetic measurements, whereas for crystallographic studies, concentrated aliquots (1-1.5 mL) were treated with thrombin (0.5 U, 4° C., overnight shacking) and cleaved 6×-His Tag was removed by gel filtration in a Superdex 200 10/30 GL. Pure protein, as judged by UV chromatogram and SDS-PAGE was concentrated to 77 mg/mL and stored at −80° C.

For screening and characterization of ADHs, a panel of alcohol dehydrogenases enzymes as freeze-dried cell free extracts in 96-deep well plates were kindly supplied by c-LEcta GmbH (Leipzig, Germany). For a first screening, each freeze-dried extract was resuspended in 50 µL of 50 mM sodium phosphate buffer pH=7.2, 100 mM KCl, and reaction carried out on a 500 µL scale with both 10 mM (R)- and (S)-HIP, 0.5 mM of both NAD+ and NADP+ and acetone 5% v/v (30° C.).

Then, best hits were chosen for a further screen on a 500 µL scale with 10 mM (R)-HIP, 0.5 mM NADP+ and acetone 5% v/v. Reaction mixtures were extracted with methyl-tert-butyl ether (MTBE), vortexed for 30 s and centrifuged 5 minutes before removing the organic layer, which was then transferred to fresh tubes containing $MgSO_4$. Finally, 250 µL of the MTBE extract was taken for chiral normal phase HPLC analysis.

For protein crystallization and docking experiments, native Cm-ADH10 was crystallized at 293 K using the sitting-drop vapour diffusion technique at 20° C. Equal volumes of 12 mg/mL Cm-ADH10 in 20 mM Tris-HCl at pH 7.5 and reservoir solution were mixed. The reservoir solution contained 40% polyethylene glycol (PEG) 200 in 0.1 M MES at pH 6.5 (w/v). Initial conditions were screened using the JSCG, PEG and ammonium sulphate screens (Qiagen) in 96-well sitting drop trays. X-Ray diffraction data were collected at the ID23-2 beamline of the European Synchrotron Radiation Facility in Grenoble, France (ESRF). The images were integrated and scaled using MOSFLM (Battye et al., Acta Crystallogr. Sect. D Biol. Crystallogr. 2011, 67, 271-281). Intensities were merged and converted to amplitudes with Aimless (Evans and Murshudov, Acta Crystallogr. Sect. D Biol. Crystallogr. 2013, 69, 1204-1214) and other software of the CCP4 Suite (Winn et al., Acta Crystallogr. Sect. D Biol. Crystallogr. 2011, 67, 235-242). The structure was solved with MOLREP (Vagin and Teplyakov, J. Appl. Cryst 1997, 30, 1022-1025) and the coordinates of the dehydrogenase/reductase from Sinorhizobium meliloti 1021 (PDB: 3V2G) as the search model. AutoDock Vina (Trott and Olson, supra) was used to run ligand-receptor docking calculation of (R)-HIP on Cm-ADH10. Structures were prepared with DockPrep (Lang et al., Rna 2009, 1219-1230) in Chimera. The best model yielded a score of −5.6 kcal/mol, a rmsd (l.b) of 0.0 and a rmsd (u.b.) of 0.0.

Example 2: Screening and Improvement of P450cam-RhFRed Variants

A plasmid library encoding 96 P450cam-RhFRed mutants generated in a previous work (Kelly et al., Beilstein J. Org. Chem. 2015, 11, 1713-1720) were purified from bacterial glycerol stocks. P450cam-RhFRed variants were produced targeting 7 pairs of residues by saturation mutagenesis using NDT codon degeneracy. This resulted in the production of seven libraries: A to F (see Table 2). In order to cluster these variants, 100 ng of each plasmid purified were added to one of five pools according to the mutations introduced, the exceptions being variants from library E, F and G that were pooled together because the reduced size of these libraries (giving five pooled libraries in total). These plasmids preparations were then transformed into E. coli NEB-5-alpha competent cells and plasmids purified again for transformation into E. coli BL21 (DE3) for expression. FIG. 2 shows the measured biocatalytic performance expressed in terms of the total TTN, that is the ratio between total product concentration (in μM) and catalyst concentration (in μM), calculated over 24 h. Finally, the enantiomeric excess values (ee) were also determined by comparison with synthesized standards (see Table 2). The P450-catalysed single oxidation of α-IP may lead to (at least) three major products (FIG. 1B): HIP (6), the regioisomeric allyic oxidation product (3-(hydroxymethyl)-5,5-dimethylcyclohex-2-en-1-one, HMIP, 7) and isophorone oxide (2,3-epoxy-3,5,5-trimethyl-1-cyclohexanone, IPO, 8). Product 7 was identified after scale up and NMR analysis (not shown). The formation of isophorone oxide was not observed and (R)-HIP was the preferred product (FIG. 1B), with library D (mutations at residues L244-V247) showing the highest TTNs in the desired α-IP allytic oxidation. Notably, no activity was detected for mutants in pool C (mutations at residues M184-T185).

TABLE 2

Possible products of the P450 oxidation of α-IP and comparison of (R)-HIP ee values for the different pooled mutation libraries, "nd" means "not detectable".

| Pool | Position of mutation | (R) HIP ee value |
|---|---|---|
| EFG | G248-T252; V295-D297; I395-V396 | 77% |
| D | L244-V247 | 94% |
| C | M184-T185 | n.d. |
| B | F98-T101 | 48% |
| A | F87-F96 | >99% |

These initial results drove the next step of the investigation towards the single-clone level analysis of mutants at positions L244-V247.

Expression cultures were centrifuged (2831 g, 20 min, 4° C.) and the pellet resuspended to 230 mg/mL (wet weight) in the appropriate biotransformation buffer (50 mM sodium phosphate buffer, pH=7.2, 100 mM KCl).

Biotransformations were carried out in 48 well plates on a 1 ml scale, with 880 μL of re-suspended cells, 100 μL of 100 mg/mL glucose and the appropriate final concentration of substrate typically added from concentrated stocks in DMSO (2% v/v final concentration). Plates were sealed with a gas permeable membrane and reaction carried out with 250 rpm orbital shaking for 24 h. Reaction mixtures were extracted with 1 mL of methyl-tert-butyl ether (MTBE) with 1 mM decane (as internal standard) vortexed for 30 s and centrifuged 5 minutes before removing the organic layer, which was then transferred to fresh tubes containing $MgSO_4$. Finally, 250 μL of the MTBE extract was taken for GC analysis and diluted when necessary. In order to determine the ee %, the samples were also analyzed by chiral normal phase HPLC (see Ex. 1).

Analysis of biotransformation products (FIG. 3) demonstrated that positions 244 and 247 greatly affect TTNs of α-IP. Interestingly, the majority of mutants bearing the bulky aromatic phenylalanine residue show not only reduced TTNs but also a decrease in the regioselectivity of the reaction, with the formation of HIP and HMIP in approximately equal amounts by mutants L244Y-V247F and L244I-V247F. Given the observed positive effect of the substitution of L244 with small or apolar residues, the mutation L244A was also introduced, considering the effect of L244A mutation on substrate acceptance, regio- and enantioselectivity. The primers for said mutagenesis reactions are listed in Table 1. The protocol is described in Example 1. The protein and DNA sequences of P450cam-RhFRed wild-type enzyme carrying the amino acid substitution Y96F are shown in SEQ ID NO:1 and 2, respectively.

This mutation was studied either in presence of the wild-type V247 or V247L, leading to good TTNs values. The two mutants L244A-V247 and L244A-V247L showed the best TTN values (94±9 and 83±11, respectively) and were selected for further engineering. Furthermore, the bulky tryptophan was introduced in place of phenylalanine at position 87. As shown in Table 3, the introduction of F87W in the L244A-V247L background led to more than a 6-fold improvement of TTNs values with respect to L244A-V247L mutant, with no HMIP detected and an ee of 99% (R)-HIP, suggesting a better orienting effect of this biocatalyst towards the highly reactive iron-oxo species. Finally, the best improved variant (Y96F-F87W-L244A-V247L, now termed P450-WAL) was selected for subsequent optimization experiments for the designed cascade reaction (see Example 1) The results are shown in Table 3.

TABLE 3

(R)-HIP ee values obtained for different mutations from library D. Note that the strain already carries the Y96F mutation.

| Mutant | (R) HIP ee value |
|---|---|
| L244N-V247 | 94% |
| L244S-V247L | 99% |
| L244N-V247L | 99% |
| L244G-V247L | 99% |
| L244I-V247L | 98% |
| L244C-V247L | 98% |
| L244I-V247F | 95% |
| L244Y-V247F | 93% |
| L244N-V247F | 98% |
| L244H-V247F | 99% |
| L244G-V247F | 96% |
| L244I-V247I | 98% |
| L244I-V247S | 59% |
| L244A-V247L | 97% |
| L244A-V247 | 84% |
| F87W-L244A-V247 | 82% |
| F87-L244A-V247L | 99% |

Example 3: Screening and Characterization of HIP-Oxidizing ADHs

A screening kit of 116 ADHs from very diverse organisms and with a broad range of accepted substrates was provided by c-LEcta. In order to identify suitable biocatalysts for the oxidation of (R)-HIP, the panel was screened against this substrate by HPLC (see Example 1). Several enzymes (>80%) showed almost no activity, due to the steric hindrance of the substrate, however, among the positive hits, two were selected for having the highest activity: Cm-ADH10 from *Candida magnoliae* (GeneBank accession no. AGA42262.1; SEQ ID NO:5) and the NADPH-dependent carbonyl reductase (SSCR) from *Sporobolomyces salmonicolor* (UniProt accession no. Q9UUN9; SEQ ID NO:7). Notably, both enzymes accept NADP(H) as cofactor, which is desirable to create a self-sufficient cascade with respect to the cofactor. The corresponding genes were cloned into a pET28a vector to carry out expression trials (see Example 1), which revealed good expression levels for Cm-ADH10. Unfortunately, expression of SSCR was very low (not shown). The respective nucleotide acid sequences are shown in SEQ ID NO:6 and 8, respectively.

To understand better the catalytic properties of Cm-ADH10, we solved the crystal structure of its complex with NADP+ to a resolution of 1.6 Å (see Example 1; data not shown). After soaking the crystal with a solution of (R)-HIP (10 mM), no substrate was bound to the crystal. However, after docking (AutoDock Vina), the most favored calculation for the bound ligand (R)-HIP confirms that the cavity can accommodate the substrate at a distance and geometry that would favor the transfer of a hydride from the chiral carbon on the 4R-hydroxy moiety to C4N of NADP+. In this position, the 4-hydroxy group would be in the right geometry to interact with the catalytically important residues S144 and Y157, while the rest of the molecule of 4R-HIP is possibly stabilized by interactions with residues H149 and Y189 in the entrance of the active site. Coincidentally, this area in the crystal structure is occupied by a tetrad of water molecules that have been reported to be bound to the Tyr-OH and Lys side chain, thus mimicking substrate and ribose hydroxyl group positions.

Preliminary biotransformations by varying (R)-HIP concentration from 10 to 100 mM were carried out, using 1 mg ml−1 purified Cm-ADH10 with a constant NADP+ concentration (0.25 mM) and 0.5% v/v ethyl acetoacetate as co-substrate for cofactor regeneration by the same ADH acting as a dual-functional enzyme. With this setup, conversions ranged from 92% with 10 mM substrate, down to 48% conversion with 100 mM substrate (see FIG. 4). Thus, Cm-ADH10 lends itself to being applied in the designed bi-enzymatic cascade.

Example 4: Optimization of Buffer Concentration, pH, and Temperature

Initially, we tried to combine the two selected biocatalysts in a one-pot, two-step format, adding 1 mg mL$^{-1}$ of purified Cm-ADH10, cofactor and co-substrate (see above) directly to the supernatant of the whole-cell P450 reaction carried out with 200 mg mL$^{-1}$ wet cell load in 50 mM sodium phosphate buffer pH 7.2, 100 mM KCl (indicated as standard biotransformation buffer) and 10 mg mL$^{-1}$ glucose for cofactor regeneration by *E. coli* metabolism. Unexpectedly, we obtained very low conversion values for the ADH catalyzed reaction, starting from just 10 mM α-IP in the first step. We reasoned that potential inhibitors for the second step could originate from the growth of the whole-cell biocatalysts in the M9 minimal medium supplemented with glucose (see FIG. 5A). The pH of the supernatant resulting from the first oxidation step carried out in phosphate buffer with different concentration was measured (FIG. 5B). Surprisingly, the pH dropped by 1.5 units when the standard biotransformation buffer was used, and even with a 300 mM potassium phosphate (KPi) buffer the pH decrease was significant. Nevertheless, by increasing the capacity of the buffer employed in the first step, higher conversions where observed in the second one. Eventually, more than a 2-fold increase in HIP conversion was observed when P450 catalyzed reaction carried out in standard biotransformation buffer were titrated to pH 8.0 before the addition of Cm-ADH10. A similar trend was observed when cells grown in M9 medium where simply resuspended in buffer without any addition of substrate or glucose, suggesting that the observed pH decrease is linked to the metabolism of cells grown to high density (OD600~5.0-6.5). Thus, in order to establish a one-pot two-step process there is a need for a careful optimization of the each individual step before combination.

Next, we proceeded with the parallel optimization of the two oxidative steps with respect to buffer concentration, pH and temperature. For the P450 allylic oxidation step, KPi buffer (pH 8.0) was chosen for the unique K+ binding site of P450cam, which displays higher stability and superior camphor binding in presence of K+ ions. The effect of buffer concentration was examined, along with the temperature optimum. As shown in FIG. 6A, conversion improved with increasing buffer concentration up to 200-300 mM, and by comparing biotransformations carried out in 50 mM KPi without KCl, with KCL or in 100 mM KPi, it can be concluded that buffer capacity seems to have a greater effect on conversion than K+ concentration. Eventually, 200 mM $KP_i$ buffer was chosen to investigate the effect of temperature on conversion, finding the optimum at 28° C. (FIG. 6B).

With respect to the Cm-ADH10 alcohol oxidation, different co-substrates were selected and tested in order to exploit the biocatalyst as a dual-functional enzyme capable of performing the whole substrate oxidation-cofactor regeneration cycle (FIG. 7A). Besides testing acetone (9a), we have also included activated ketones such as chloroacetone (9b), ethyl acetoacetate (9c) and ethyl levulinate (9d), since their reduction (and hence cofactor regeneration) is favored by an additional intramolecular hydrogen bond between the newly formed alcohol functional group and the electronegative moiety.

Chloroacetone and ethyl acetoacetate proved to be superior and, even if the latter performed better during the first six hours of reaction, the former pushed the conversion to 84% with 40 mM substrate after 24 h (vs. 67% with ethyl acetoacetate). Therefore, chloroacetone was employed as hydrogen acceptor in all the subsequent optimization steps. The pH effect on the reaction outcome (FIG. 7B) partially explains our initial unsuccessful attempts to combine the two enzymes: in fact, enzyme activity drops below pH 6.0, with an optimum pH range between 7.0 and 9.0. Moreover, the buffer system employed in the P450 catalyzed reaction (200 mM KPi) displayed perfect compatibility with the second step (FIG. 8). Finally, we turned our attention to temperature optimization, finding the highest conversion at 40° C. (FIG. 7C).

With these optimized conditions in hand, we moved on to the envisaged bi-enzymatic cascade concept to carry out scale-up experiments for product isolation and characterization.

Example 5: Double Oxidation from α-Isophorone to Ketoisophorone

In order to further simplify the entire process, the oxidation of (R)-HIP was accomplished using a concentrated cell-free extract (CFE) of *E. coli* overexpressing Cm-ADH10, thus avoiding the expensive protein purification step. The course of the reaction under the optimized conditions was followed over a total reaction time of 50 h, showing that the P450 catalyzed allylic oxidation of 10 mM α-IP reached 94±2% conversion in 18 h, whereas the second step was much faster, reaching complete conversion over 6 h (FIG. 9). Remarkably, the addition of NADP+ for the second step was found to be unnecessary to achieve the highest conversion, further reducing process costs. Some degree of overoxidation of HIP to KIP was observed during the first step.

Given these results, we have also attempted to co-express the P450cam-RhFRed-WAL variant with Cm-ADH10 in the same host with a two-vector system to carry out the whole-cell double oxidation of α-IP (FIG. 1D). After 24 h, the conversion reached an average value of 73±2%, approximately 20% lower than for the one-pot two-step process. However, the co-expression of the two enzymes and cofactor preferences make this reaction redox-balanced, avoiding addition of a CFE and co-substrate. In fact, P450 expression level was reduced 3-fold in the "designer" microorganism (6.0 μM for the two-step process vs. 1.9 μM for the whole-cell process), which accounted for the residual α-IP (not shown).

The invention claimed is:

1. A biocatalytic process for the conversion of α-isophorone into ketoisophorone (KIP) comprising the enzymatic steps of:
   (a) converting α-isophorone into 4-hydroxy-α-isophorone (HIP) via catalytic action of a P450 monooxygenase wherein
      1) at least 80% of α-isophorone is converted into HIP;
      2) the P450 monooxygenase comprises
         i. a first polypeptide having at least 90% identity to SEQ ID NO:1 or
         ii. a second polypeptide having at least 62% identity to SEQ ID NO:3, said second polypeptide comprising an F at position 97 according to SEQ ID NO:3 and one or more substitutions at positions 88, 245, and 248 according to SEQ ID NO:3, wherein said one or more substitutions comprise F88W, L245X, and V248X, wherein "X" is any amino acid; and wherein the total turnover number of the second polypeptide is increased by at least 2-fold compared to a reference P450 monooxygenase according to SEQ ID NO: 3; and
   (b) converting the HIP from (a) into KIP via catalytic action of an enzyme having alcohol dehydrogenase or carbonyl reductase activity, wherein at least 40% of HIP is converted into KIP.

2. A process according to claim 1, wherein the process is characterized by one or both of
   (a) the biocatalytic process for the conversion of α-isophorone to 4-hydroxy-α-isophorone (HIP) is carried out in the presence of a co-substrate selected from the group consisting of glucose, isopropanol and phosphite; and
   (b) the biocatalytic process for the conversion of HIP to KIP is carried out in the presence of a co-substrate selected from the group consisting of acetone, chloroacetone, ethyl acetoacetate, ethyl levulinate, chloroacetone and ethyl acetoacetate.

3. A process according to claim 1, which is characterized by one or both of
   (a) the enantiomeric excess towards the (R)-configuration of HIP generated via the biocatalytic process is at least 50% based on the total amount of HIP; and
   (b) the enantiomeric excess towards the (R)-configuration of KIP generated via the biocatalytic process is at least 50% based on the total amount of KIP.

4. The process according to claim 1, which is a one-pot process performed under incubation conditions of pH of from 4.0 to 10.0 for 1 to 48 h.

5. A process according to claim 4 which is performed at a temperature of 30° C. to 40° C.

6. The process of claim 1, wherein the P450 monooxygenase comprises the second polypeptide.

7. The process of claim 1, wherein the second polypeptide comprises the amino acid substitutions of F88W, L245X, and V248X, wherein "X" is any amino acid.

8. The process of claim 1, wherein the second polypeptide comprises the amino acid substitutions of (i) F88W, and L245A or (ii) F88W, L245A, and V248L.

9. The process of claim 1, wherein (a) further comprises isolating HIP from the reaction mixture.

10. The process according to claim 1, wherein the enzyme having alcohol dehydrogenase or carbonyl reductase activity catalysing the conversion of HIP into KIP is selected from an alcohol dehydrogenase from Candida magnoliae or a carbonyl reductase from Sporobolomyces salmonicolor.

11. The process of claim 1, wherein (b) further comprises isolating KIP from the reaction mixture.

12. A process for the production of vitamin E, comprising the step of biocatalytic conversion of α-isophorone into KIP according to claim 1.

* * * * *